United States Patent
Namisaki et al.

(10) Patent No.: US 11,419,878 B2
(45) Date of Patent: Aug. 23, 2022

(54) MEDICINE OBTAINED BY COMBINING FXR AGONIST AND ARB

(71) Applicant: Intercept Pharmaceuticals, Inc., New York, NY (US)

(72) Inventors: Tadashi Namisaki, Nara (JP); Hitoshi Yoshiji, Nara (JP)

(73) Assignee: Intercept Pharmaceuticals, Inc., Morristown, NJ (US)

( * ) Notice: Subject to any disclaimer, the term of this patent is extended or adjusted under 35 U.S.C. 154(b) by 0 days.

(21) Appl. No.: 16/089,274

(22) PCT Filed: Mar. 27, 2017

(86) PCT No.: PCT/JP2017/012448
§ 371 (c)(1),
(2) Date: Sep. 27, 2018

(87) PCT Pub. No.: WO2017/170434
PCT Pub. Date: Oct. 5, 2017

(65) Prior Publication Data
US 2019/0247404 A1    Aug. 15, 2019

(30) Foreign Application Priority Data
Mar. 28, 2016 (JP) .............................. JP2016-064475

(51) Int. Cl.
*A61K 31/575*    (2006.01)
*A61P 1/16*      (2006.01)
(Continued)

(52) U.S. Cl.
CPC ............ *A61K 31/575* (2013.01); *A61K 31/41* (2013.01); *A61K 31/4178* (2013.01);
(Continued)

(58) Field of Classification Search
CPC .... A61K 31/575; A61K 45/06; A61K 31/454; A61K 31/42; A61K 31/4184;
(Continued)

(56) References Cited

U.S. PATENT DOCUMENTS

| 7,786,102 | B2 | 8/2010 | Pellicciari |
| 9,238,673 | B2 | 1/2016 | Steiner et al. |
| 9,498,484 | B2 | 11/2016 | Fiorucci et al. |

FOREIGN PATENT DOCUMENTS

| WO | WO 2002/072598 A1 | 9/2002 |
| WO | WO 2008/002573 A2 | 1/2008 |

(Continued)

OTHER PUBLICATIONS

Neuschwander-Tetri, Farnesoid X nuclear receptor ligand obeticholic acid for non-cirrhotic, non-alcoholic steatohepatitis (FLINT): a multicentre, randomised, placebo-controlled trial, Lancet, 2015, 385, pp. 956-965 (Year: 2015).*

(Continued)

*Primary Examiner* — Savitha M Rao
*Assistant Examiner* — Andrew P Lee

(57) ABSTRACT

The present invention provides an NASH therapeutic agent including: an FXR agonist, preferably obeticholic acid or a pharmaceutically acceptable salt thereof; and an ARB or a pharmaceutically acceptable salt thereof.

5 Claims, 9 Drawing Sheets

(51) Int. Cl.
| | |
|---|---|
| A61K 31/41 | (2006.01) |
| A61K 31/4178 | (2006.01) |
| A61K 31/42 | (2006.01) |
| A61K 31/454 | (2006.01) |
| A61K 45/06 | (2006.01) |
| A61K 31/4184 | (2006.01) |
| A61K 31/4245 | (2006.01) |

(52) U.S. Cl.
CPC .......... *A61K 31/4184* (2013.01); *A61K 31/42* (2013.01); *A61K 31/4245* (2013.01); *A61K 31/454* (2013.01); *A61K 45/06* (2013.01); *A61P 1/16* (2018.01)

(58) Field of Classification Search
CPC ................ A61K 31/4245; A61K 31/41; A61K 31/4178; A61K 31/46; A61K 2300/00; A61P 1/16
See application file for complete search history.

(56) References Cited

FOREIGN PATENT DOCUMENTS

| WO | WO 2009/012125 A1 | 1/2009 |
|---|---|---|
| WO | WO 2011/020615 A1 | 2/2011 |
| WO | WO 2014/142364 A2 | 9/2014 |
| WO | WO 2014/200349 A1 | 12/2014 |
| WO | WO 2015/008849 A1 | 1/2015 |

OTHER PUBLICATIONS

Yoshiji, Losartan, an angiotensin-II type 1 receptor blocker, attenuates the liver fibrosis development of non-alcoholic steatohepatitis in the rat, BMC Research Notes, 2009, 2(70), pp. 1-3. (Year: 2009).*
Bueno A. et al. "Dipeptides as Effective Prodrugs of the Unnatural Amino Acid (+)-2-Aminobicyclo[3.1.0]hexane-2,6-dicarboxylic Acid (LY354740), a Selective Group II Metabotropic Glutamate Receptor Agonist", Journal of Medicinal Chemistry, 2005, vol. 48, No. 16, p. 5305-5320.
CAS 459789-99-2, 1 page.
CAS 474-25-9, 2 pages.
CAS 1268244-88-7, 1 page.
Fujino, T. et al. "Structure-activity relationship of bile acids and bile acid analogs in regard to FXR activation", Journal of Lipid Research, 2004, vol. 45, p. 132-138.
Hoofnagle J.H. et al. "Vitamin E and changes in serum alanine aminotransferase levels in patients with non-alcoholic steatohepatitis", Alimentary Pharmacology and Therapeutics, 2013, vol. 38, No. 2, p. 134-143.
Matteoni C.A. et al. "Nonalcoholic fatty liver disease: A spectrum of clinical and pathological severity", Gastroenterology, 1999, vol. 116, p. 1413-1419.
Namisaki T. et al., "Beneficial effects of combined ursodeoxycholic acid and angiotensin-II type 1 receptor blocker on hepatic fibrogenesis in a rat model of nonalcoholic steatohepatitis", J. Gastroenterol, 2016, vol. 51, p. 162-172.
Namisaki T.et al., "Antifibrotic effects of combined treatment with farnesoid X receptor agonist and angiotensin-II type1 receptor blocker on hepatic fibrogenesis in the rat model of nonalcoholic steatohepatitis", Journal of Hepatology, 2016, vol. 64, No. 2, p. S631-S832.
Rautio J. et al. "Prodrugs: design and clinical Applications", Nature Reviews, Drug Discovery, 2008, vol. 7, p. 255-270.
Schmieder R. "Mechanisms for the Clinical Benefits of Angiotensin II Receptor Blockers", American Journal of Hypertension, 2005, vol. 18, No. 5, p. 720-730.
Siragy, H. "Evidence for Benefits of Angiotensin Receptor Blockade Beyond Blood Pressure Control", Current Hypertension Report, 2008, vol. 10, p. 261-267.
Yoshiji, H. et al. "Losartan, an angiotensin-II type 1 receptor blocker, attenuates the liver fibrosis development of non-alcoholic steatohepatitis in the rat", BMC Research Notes, 2009, vol. 2, p. 70-72.
Yoshiji, H. et al. "Angiotensin-II Type 1 Receptor Interaction Is a Major Regulator for Liver Fibrosis Development in Rats", Hepatology, 2001, vol. 34, p. 745-750.
Yoshiji, H. et al. "Angiotensin-II induces the tissue inhibitor of metalloproteinases-1 through the protein kinase-C signaling pathway in rat liver fibrosis development", Hepatology Research, 2003, vol. 27, p. 51-56.
Cariou et al. "The farnesoid X receptor (FXR) as a new target in non-alcoholic steatohepatitis", Diabetes & Metabolism, EPO Form 1703 01.91TRI, 2008, vol. 34, No. 6, pp. 685-691.
Gioiello A. et al. "Bile Acid Derivatives as Ligands ofthe Farnesoid X Receptor: Molecular Determinants for Bile Acid Binding and Receptor Modulation", Current Topics in Medicinal Chemistry, 2014, vol. 14, No. 19, pp. 2159-2174.
Namisaki Tadashi et al. "Impact of the combination of Farnesoid X receptor agonist and angiotensin-11 type1 receptor blocker on hepatic fibrogenesis in the rat model of nonalcoholic steatohepatitis", Hepatology, 2016, vol. 64, No. Suppl. 1, p. 828A, 67th Annual Meeting of the American Association for the Study of Liver Diseases (AASLO).
Neuschwander-Tetri B. A. et al. "Farnesoid X nuclear receptor ligand obeticholic acid for non-cirrhotic, non-alcoholic steatohepatitis (FLINT): a multicentre, randomised, placebocontrolled trial", Lancet, 2015, vol. 385, No. 9972, pp. 956-965.
Yokohama S.t al. "Therapeutic efficacy of an angiotensin II receptor antagonist in patients with nonalcoholic steatohepatitis", Hepatology, 2004, vol. 40, No. 5, pp. 1222-1225.
Georgescu "Angiotensin Receptor Blockers in the Treatment of NASH/NAFLD: Could They Be a First-Class Option?", Advances in Therapy, 2008, vol. 25, No. 11, p. 1141-1174.
Rizzo et al. "Functional Characterization of the Semisynthetic Bile Acid Derivative INT-767, a Dual Farnesoid X Receptor and TGR5 Agonist", Molecular Pharmacology, 2010, vol. 78, No. 4, p. 617-630.
Singh et al. "Comparative Effectiveness of Pharmacological Interventions for Nonalcoholic Steatohepatitis: A Systematic Review and Network Meta-analysis", Hepatology, 2015, vol. 62, No. 5, p. 1417-1432.
Zhang et al. "Farnesoid X receptor agonist WAY-362450 attenuates liver inflammation and fibrosis in murine model of non-alcoholic steatohepatitis", Journal of Hepatology, 2009, vol. 51, p. 380-388.
Gawrieh S. et al. "Pharmacotherapy for Nonalcoholic Fatty Liver Disease", Semin Liver Dis, 2015, 35(3):338-348.
Chou, T. -C., "Drug Combination Studies and Their Synergy Quantification Using the Chou-Talalay Method," Cancer Res, 70(2):440-446 (2010).

* cited by examiner

[Fig. 1]
Control LETO (G1)
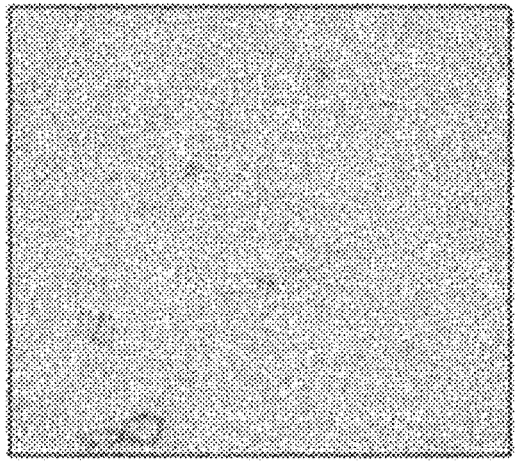
Control OLETF (G2)
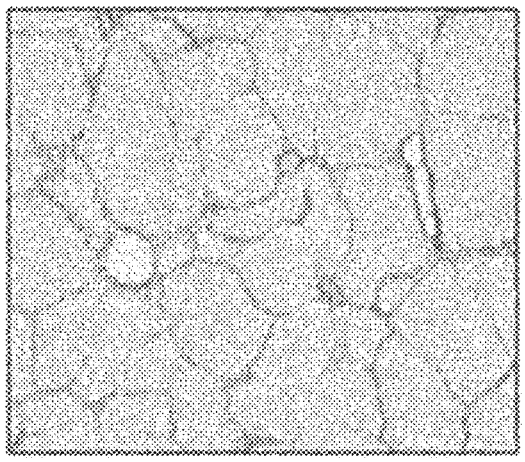
OCA-treated (G3)
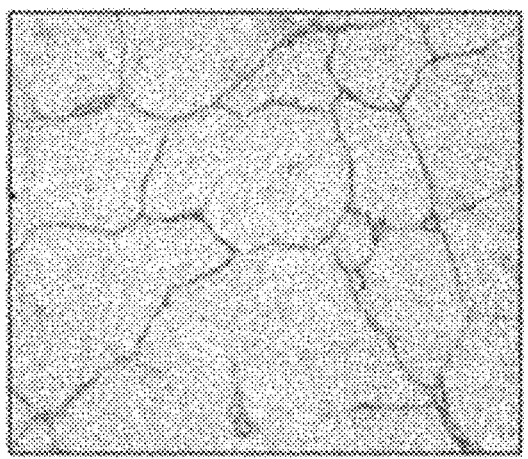
LO-treated (G4)
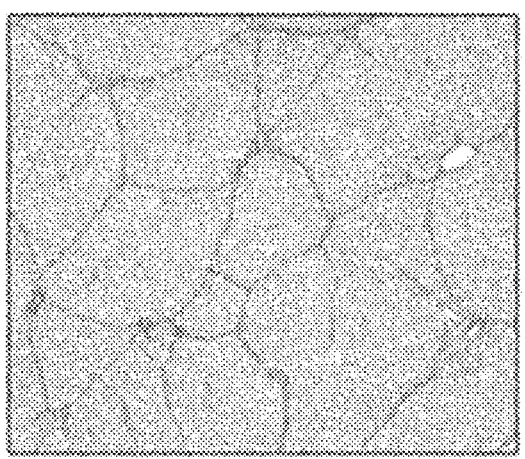
OCA+LO-treated (G5)
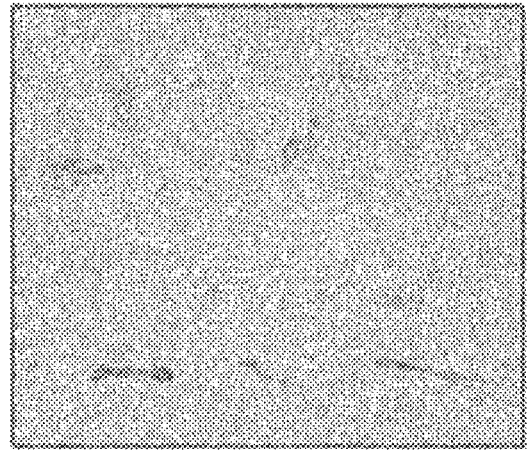

[Fig. 2]
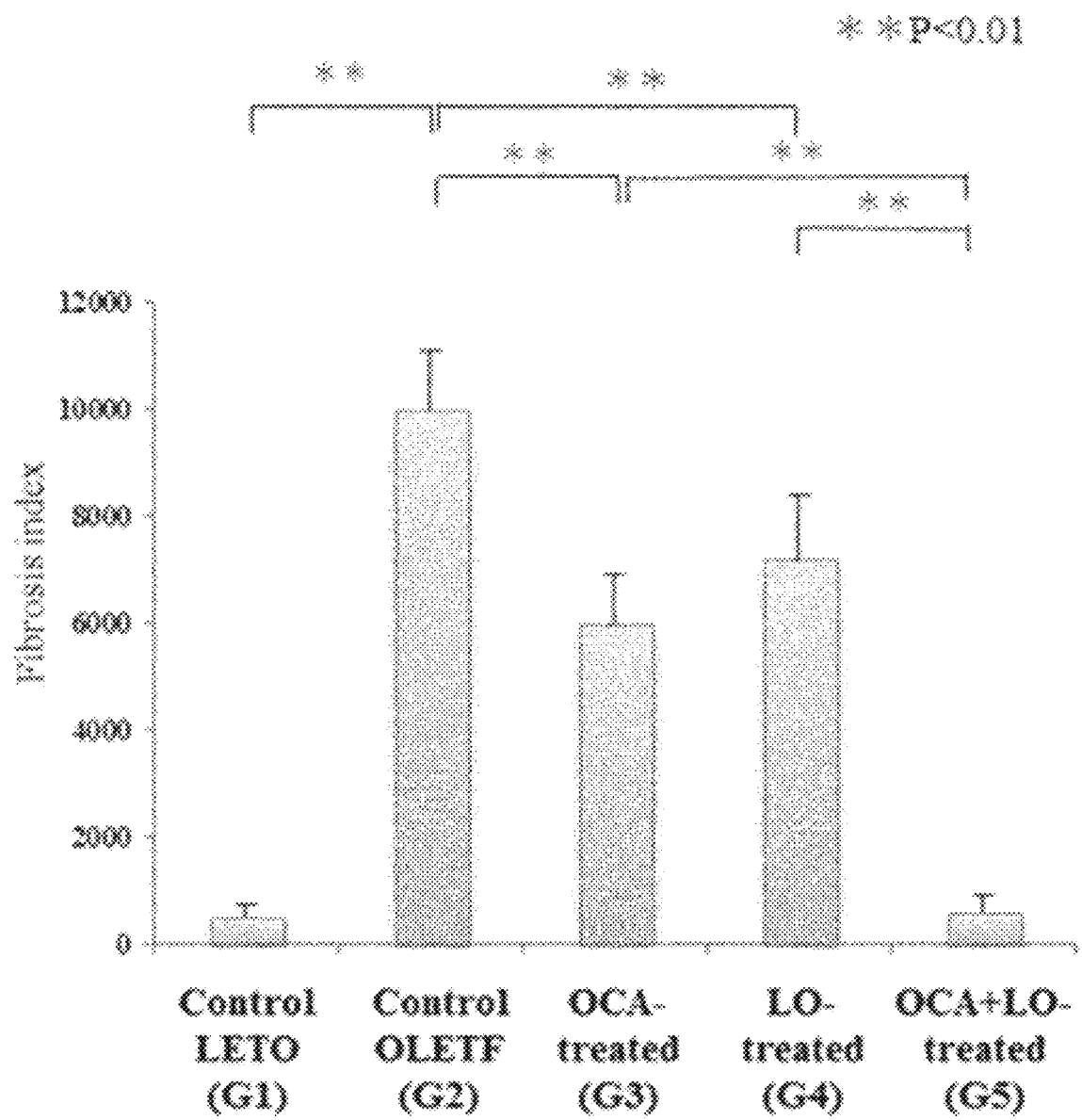

[Fig. 3]
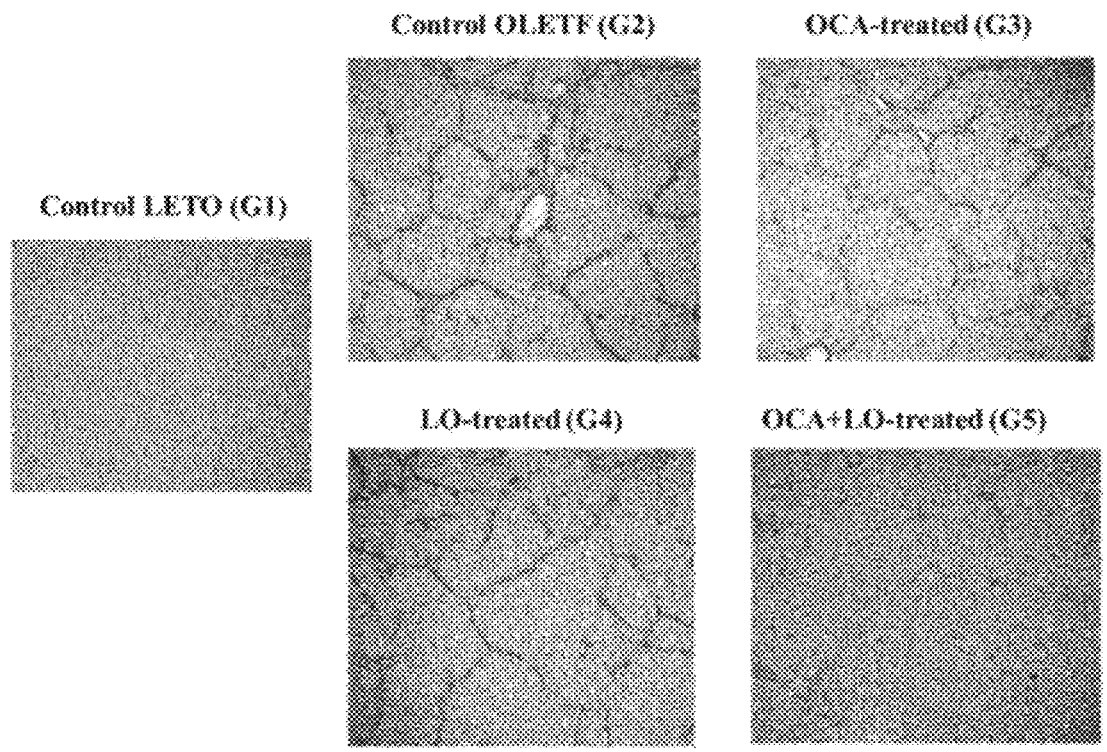
[Fig. 4]
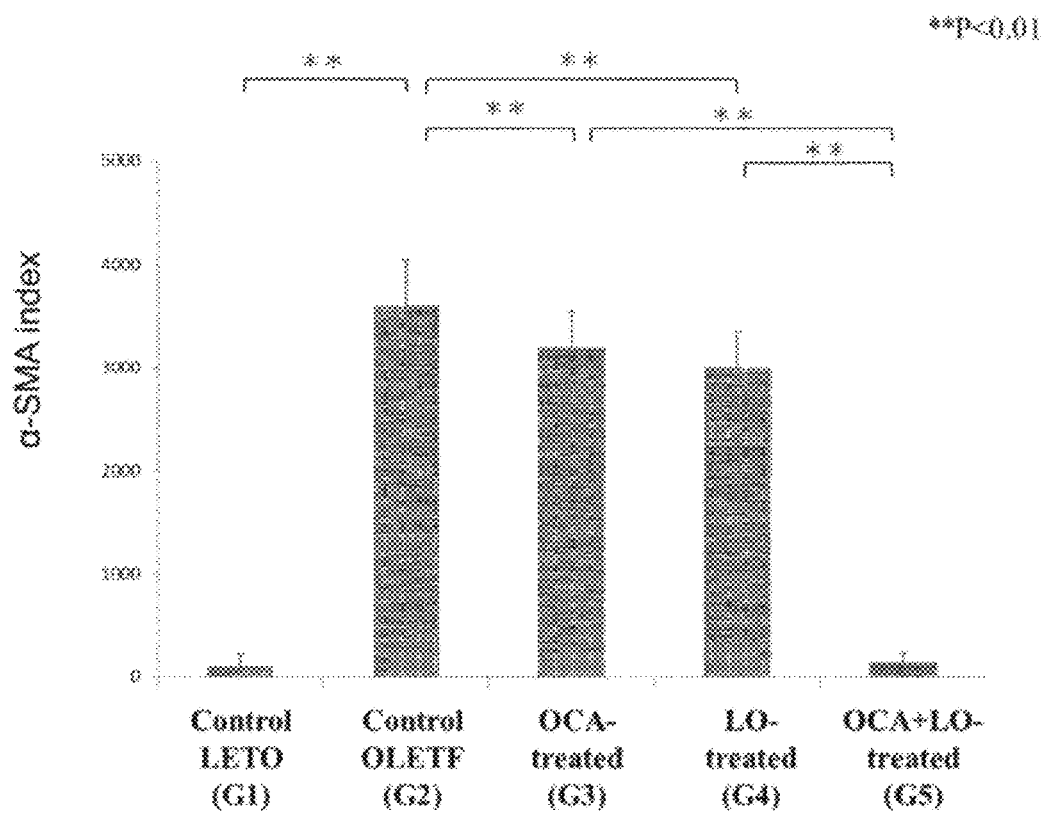

[Fig. 5]
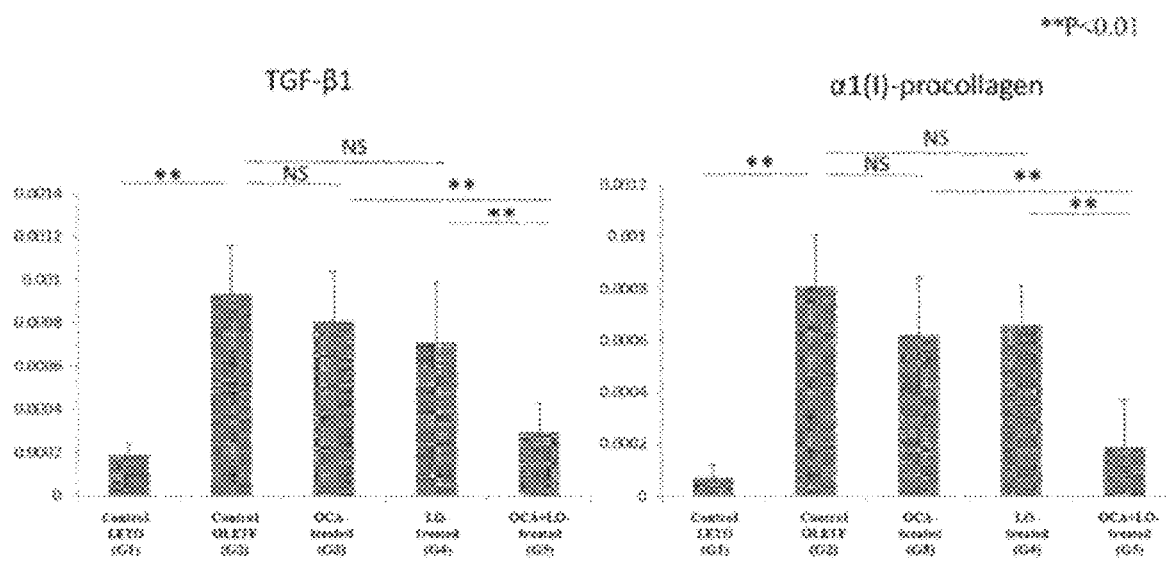
[Fig. 6]
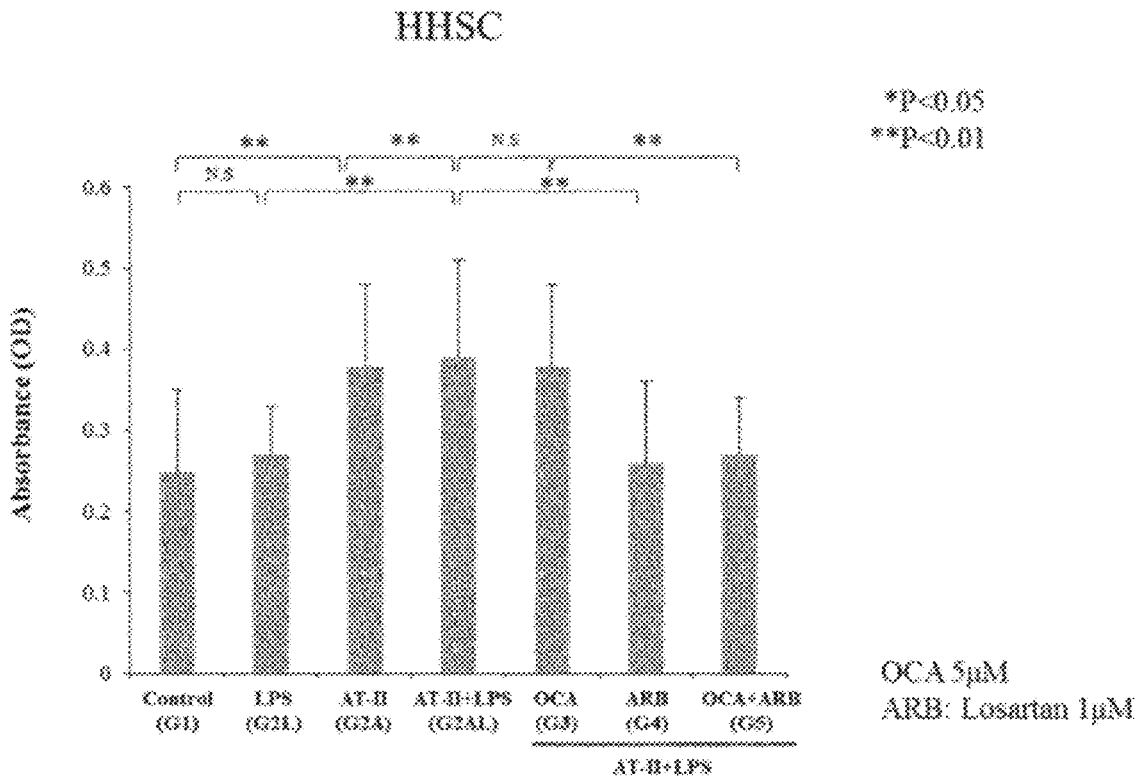

[Fig. 7]
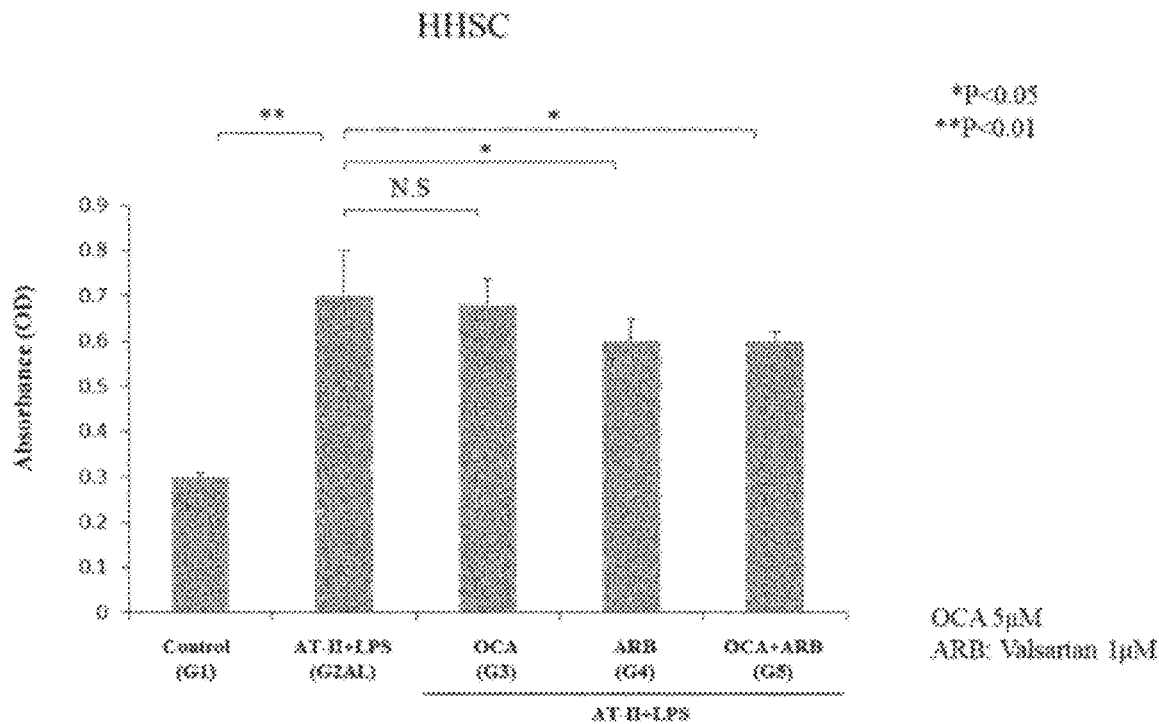
[Fig. 8]
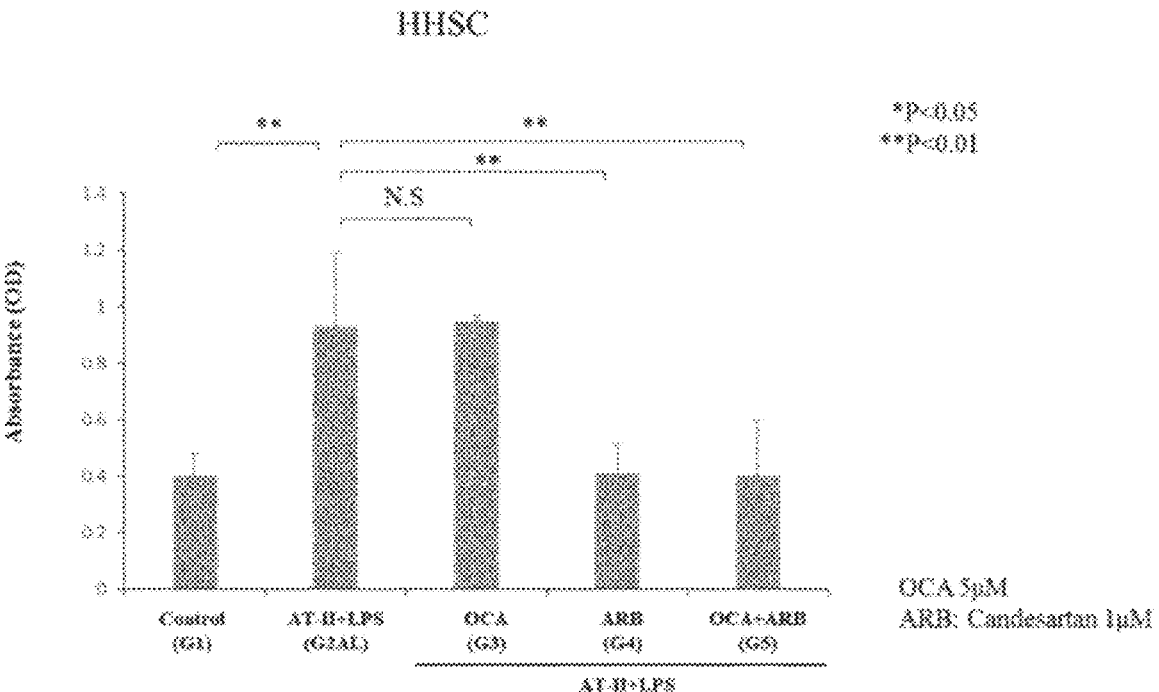

[Fig. 9]
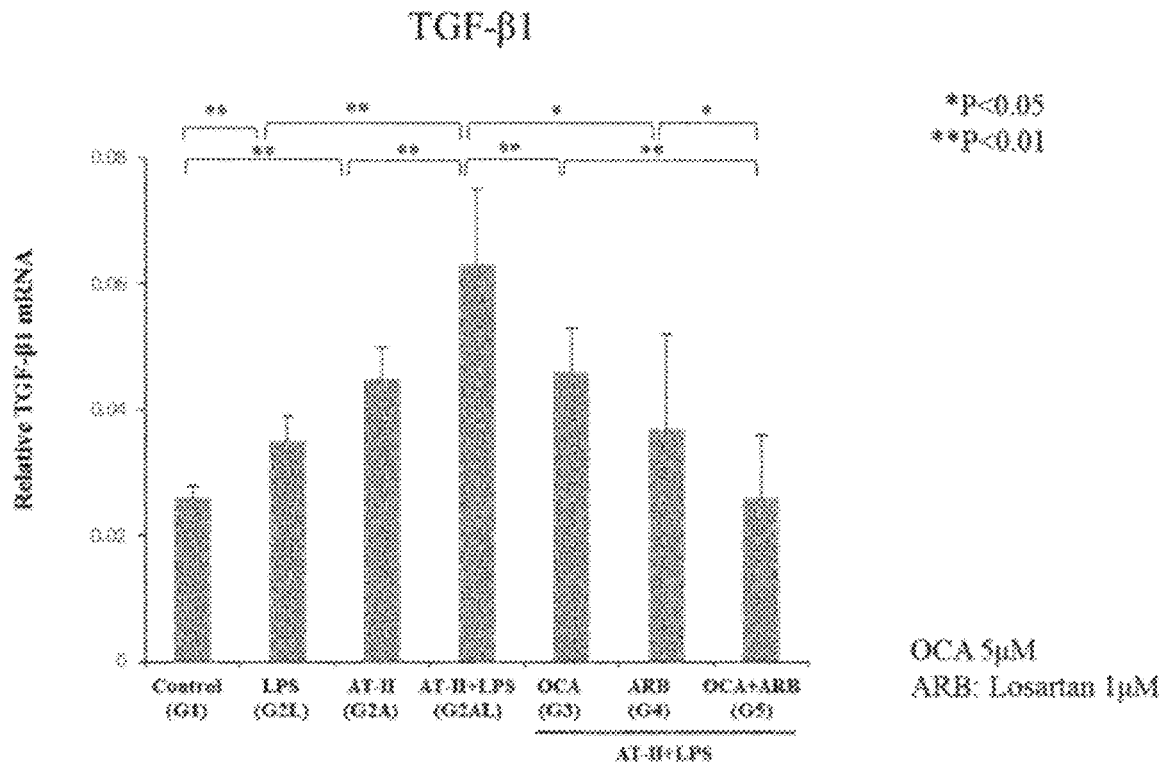
[Fig. 10]
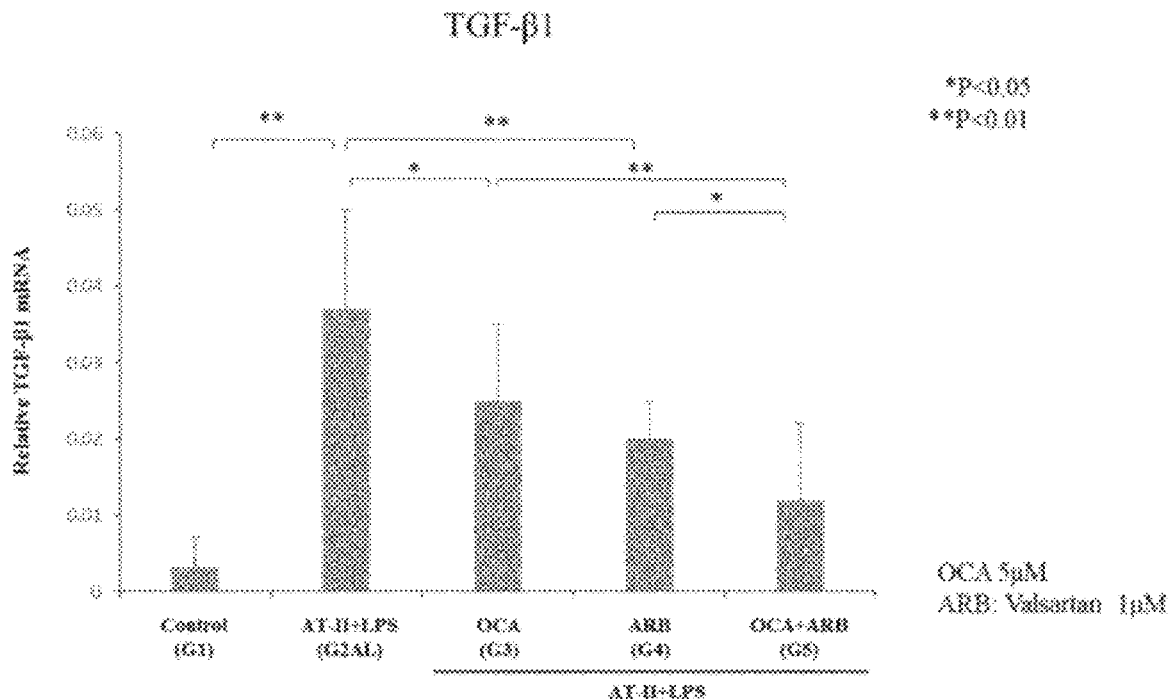

[Fig. 11]
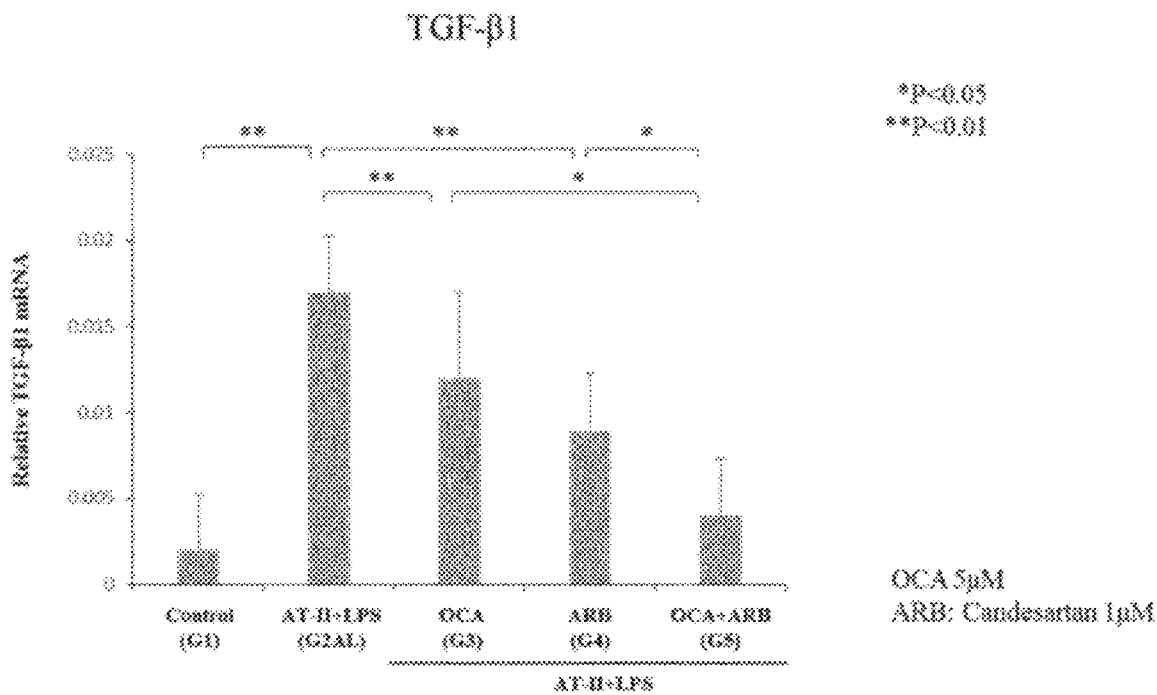
[Fig. 12]
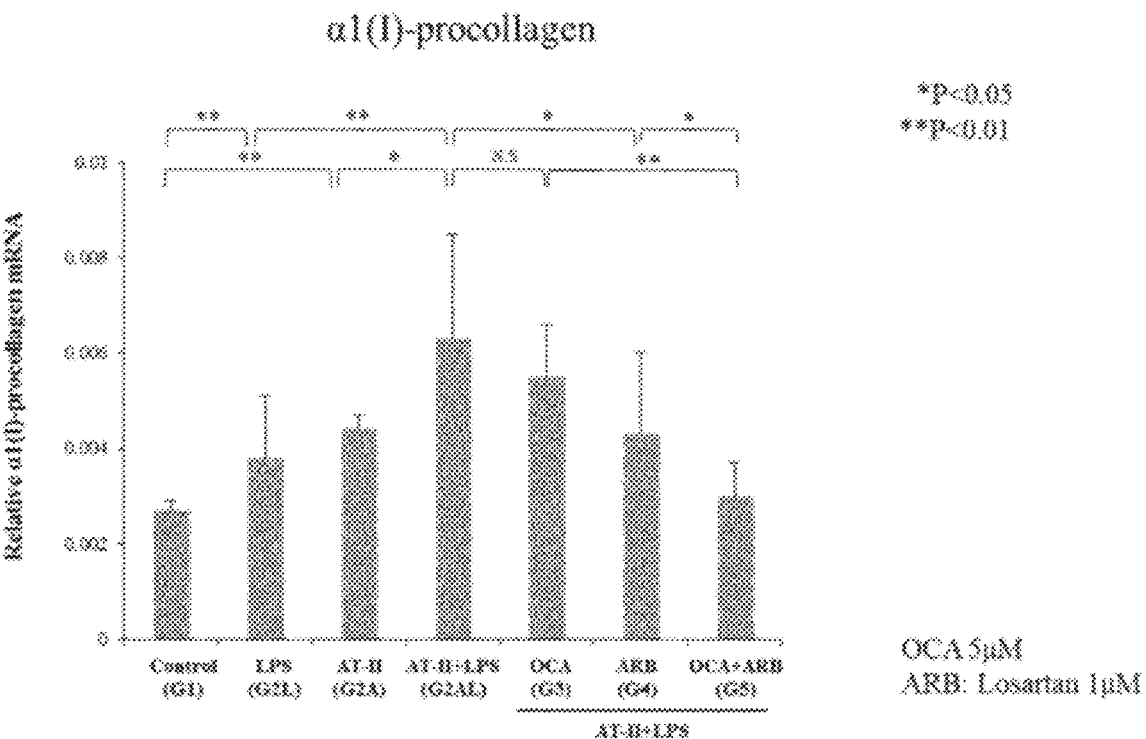

[Fig. 13]
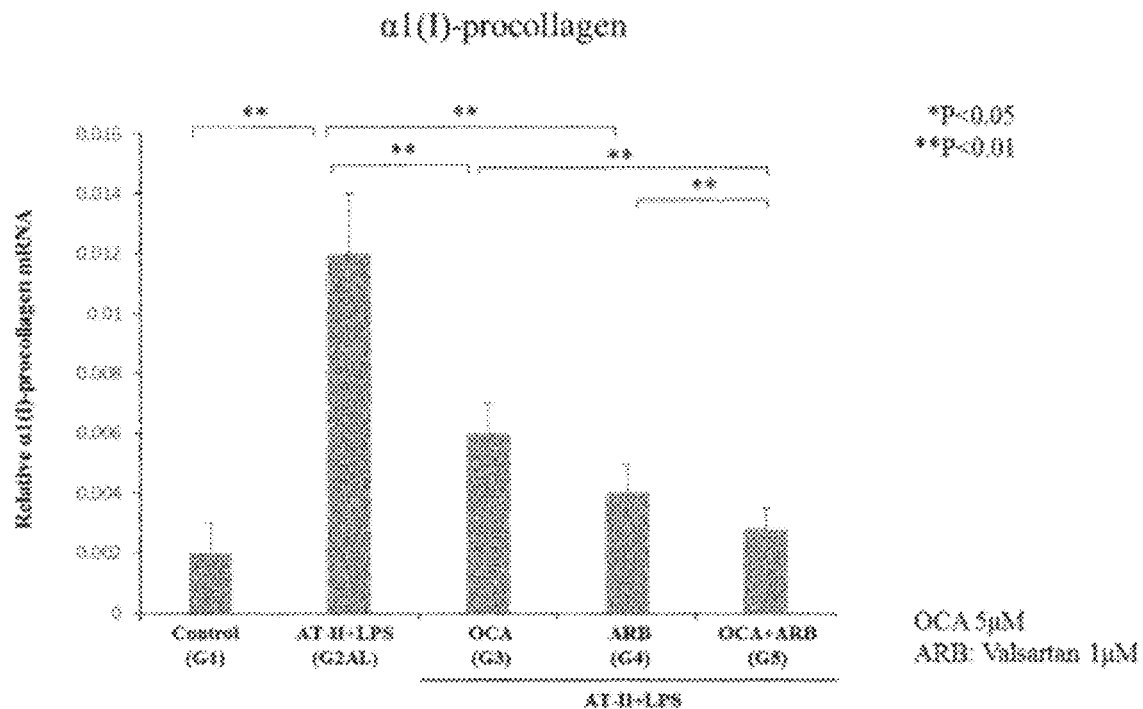
[Fig. 14]
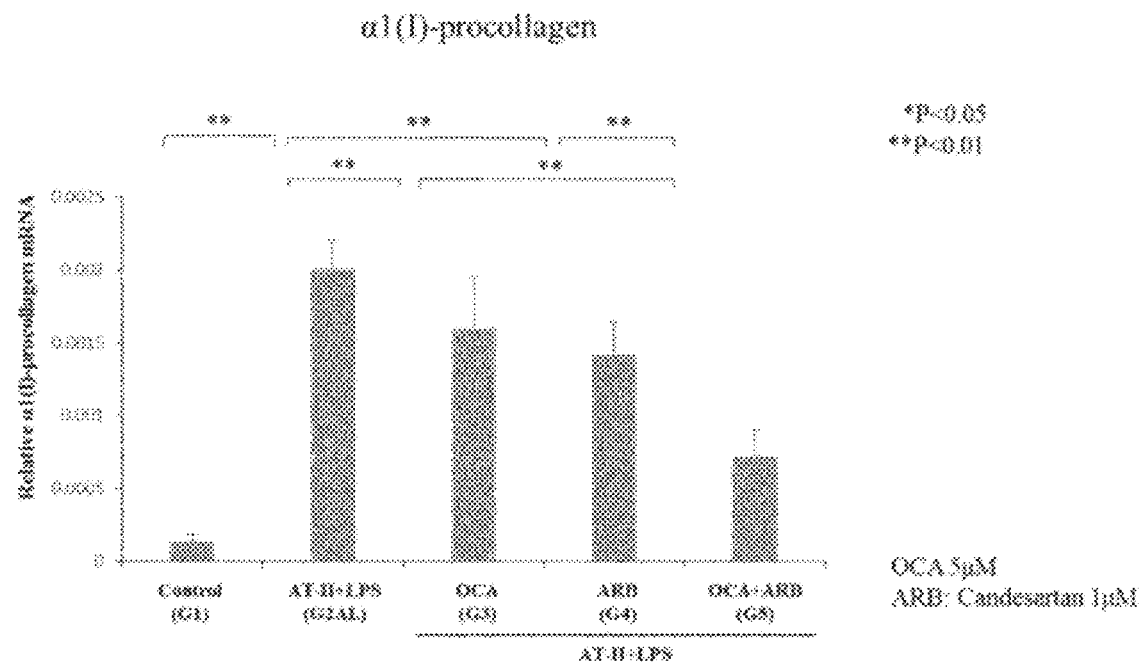

[Fig. 15]
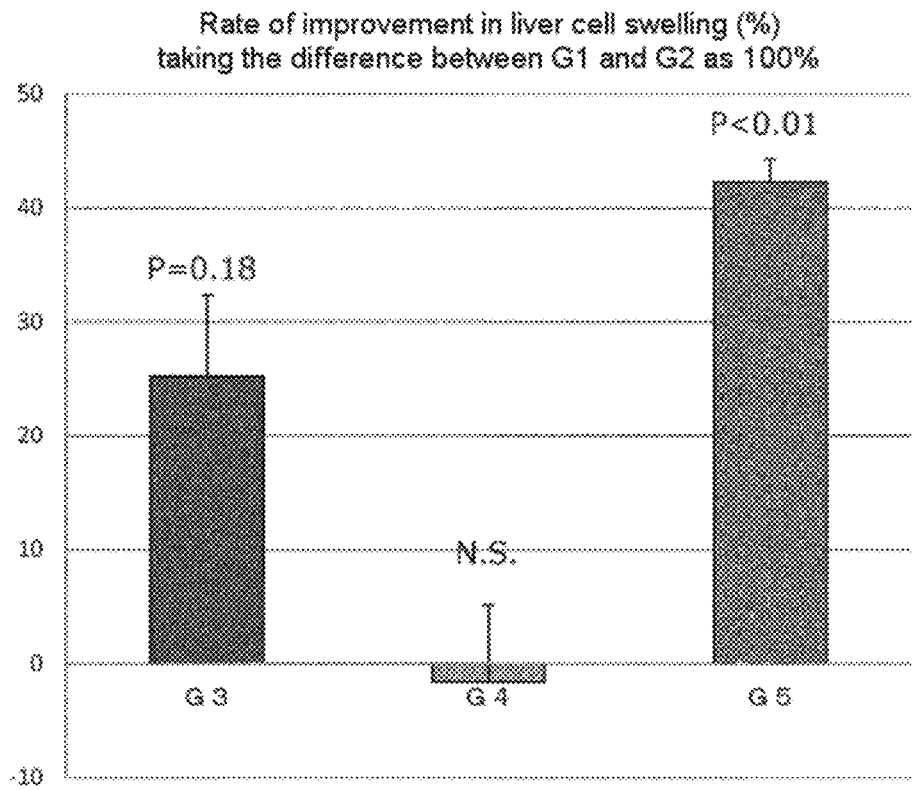
[Fig. 16]
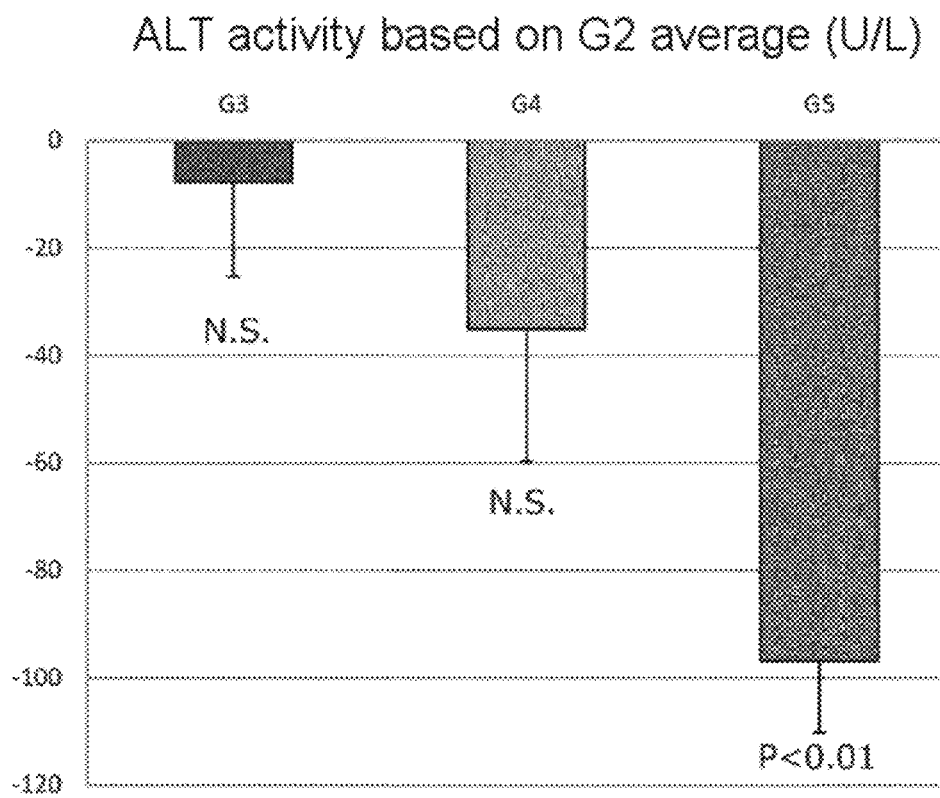

MEDICINE OBTAINED BY COMBINING FXR AGONIST AND ARB

TECHNOLOGICAL FIELD

The present invention relates to a therapeutic agent for non-alcoholic steatohepatitis (also abbreviated below as NASH in the present specification), and particularly to a therapeutic agent that is effective against hepatic fibrosis in NASH. More specifically, it relates to a therapeutic agent for NASH comprising as active ingredients a farnesoid X receptor (also abbreviated below as FXR in the present specification) agonist (particularly, obeticholic acid) or a pharmaceutically acceptable salt thereof and an angiotensin II receptor blocker (also abbreviated below as ARB in the present specification) or a pharmaceutically acceptable salt thereof.

PRIOR ART

NASH is a commonly-seen chronic liver disease characteristically occurring in metabolic disorders such as obesity and type 2 diabetes mellitus (T2DM). With the increasing prevalence of metabolic syndrome in recent years, there has been increasing interest in the prevention and treatment of various diseases resulting from metabolic syndrome. Among these diseases, NASH has been a particular focus of interest.

NASH is a type of hepatitis resulting from accumulation of fat in the liver that develops from early-stage fatty liver due to factors such as oxidative stress, insulin resistance, and inflammatory cytokines and is characterized by a transition from fatty liver disease with increasingly severe pathology. Moreover, in NASH and the progression of hepatic fibrosis secondary thereto, there is a serious risk of progression to diseases such as fatal liver cirrhosis or liver cell carcinoma.

Obeticholic acid, which has the chemical formula shown below, is currently known to have an effect in monotherapy of inhibiting fibrosis in various liver diseases, including NASH, and it is expected to be applied in treatment of diseases such as NASH and PBC (Patent Documents 1-3). Obeticholic acid is also known as 3α,7α-dihydroxy-6α-ethyl-5β-cholan-24-oic acid, 6α-ethyl-3α,7α-dihydroxy-9-cholan-24-oic acid, 6α-ethyl-chenodeoxycholic acid, 6-ethyl-CDCA, 6ECDCA, cholan-24-oic acid, 6-ethyl-3,7-dihydroxy-(3α,5β,6α,7α)-, OCA, DSP-1747, and INT-747.

[Chemical Formula 1]

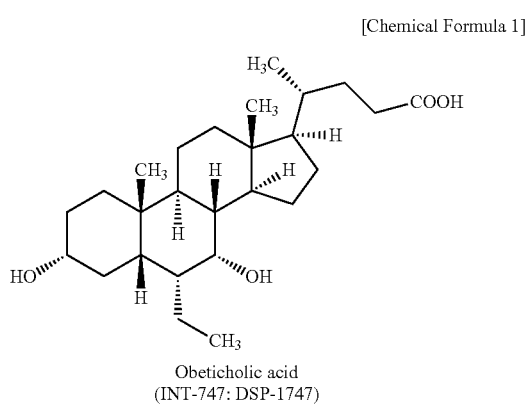

Obeticholic acid
(INT-747: DSP-1747)

ARBs, which are antagonists to the vasopressor angiotensin II, are drugs that exert an antihypertensive action by binding to the angiotensin II receptors, with examples of antihypertensives of this class in clinical use including losartan, candesartan, telmisartan, valsartan, olmesartan, irbesartan, and azilsartan. By virtue not only of their antihypertensive action, but also other actions such as reducing inflammation, improving endothelial function, inhibiting cardiovascular remodeling, inhibiting oxidative stress, inhibiting growth factors, and improving insulin resistance, ARBs are useful in the treatment of disorders such as cardiovascular disease, renal disease, and arteriosclerosis, and they have been the subject of numerous clinical and non-clinical studies (Non-Patent Documents 1-2).

With respect to ARBs, as there have also been reports that these drugs can alleviate hepatic fibrosis and that the angiotensin II receptors play a role in hepatic fibrosis, ARBs are expected to be capable of inhibiting hepatic fibrosis in liver disease (Non-Patent Documents 3-5).

Although several of these drugs, which show promise in inhibiting hepatic fibrosis in liver disease in this way, are known, virtually none of the drugs of this class have yet been found to be effective as agents for effectively preventing and treating hepatic fibrosis in liver disease, and the development of such agents is urgently needed.

Although the inventors of the present invention have reported in the past that a combination of ursodeoxycholic acid and an ARB inhibits the progress of hepatic fibrosis (Non-Patent Document 6), there have not yet been any reports on the use of a combination of an FXR agonist (particularly obeticholic acid) and an ARB in treating hepatic fibrosis in liver diseases (particularly NASH). Ursodeoxycholic acid does not have an FXR agonist action (Non-Patent Document 7).

PRIOR ART DOCUMENTS

Patent Documents

Patent Document 1: Japanese Patent No. 4021327
Patent Document 2: Japanese Patent No. 5094384
Patent Document 3: Japanese Examined Patent Application Publication No. 2015-52162

Non-Patent Documents

Non-Patent Document 1: AMER. J. Hypertension, 18, 720-730 (2005)
Non-Patent Document 2: Current Hypertension Report, 10, 261-267 (2008)
Non-Patent Document 3: BMC Res Notes; 2: 70 (2009)
Non-Patent Document 4: Hepatology, 34, 745-750 (2001)
Non-Patent Document 5: Hepatol Res, 27, 51-56 (2003)
Non-Patent Document 6: Journal of Gastroenterology, DOI: 10.1007/s00535-015-1104-x, pp. 1-11, first online: 21 Jul. 2015
Non-Patent Document 7: Journal of Lipid Research, 45, 132-138 (2004)

SUMMARY OF THE INVENTION

Object of the Invention

The object of the present invention is to provide an agent which is useful for the prevention and/or treatment of NASH, more particularly the prevention, treatment, or improvement of hepatic fibrosis in NASH, containing as its active ingredients an FXR agonist or a pharmaceutically acceptable salt thereof and an ARB or a pharmaceutically acceptable salt thereof.

Means for Achieving Object

In an effort to achieve the above object, the inventors of the present invention, taking into account in particular that NASH constitutes a complex pathology involving a variety of interconnected factors, conducted various studies in an attempt to provide effective treatment using various combinations of multiple drugs having different mechanisms of action, and as a result of extensive research, discovered that administration of a combination of an FXR agonist or a pharmaceutically acceptable salt thereof, particularly obeticholic acid or a pharmaceutically acceptable salt thereof, and an ARB or a pharmaceutically acceptable salt thereof markedly inhibited hepatic fibrosis in a model of non-alcoholic steatohepatitis (NASH) in rats, thus arriving at the present invention. More particularly, the inventors discovered that the combination of these drugs produced a therapeutic effect that was synergistically and significantly increased compared to conventional administration of obeticholic acid or an ARB in monotherapy.

Specifically, the present invention comprises the following embodiments.

[1] A combination pharmaceutical agent comprising as active ingredients a farnesoid X receptor agonist (FXR agonist) or a pharmaceutically acceptable salt thereof and an angiotensin II receptor blocker (ARB) or a pharmaceutically acceptable salt thereof.

[2] The pharmaceutical agent of [1] above, in which the FXR agonist is obeticholic acid, chenodeoxycholic acid, INT-767, Px-104 or LJN-452.

[3] The pharmaceutical agent of [1] or [2] above, in which the FXR agonist is obeticholic acid, chenodeoxycholic acid, INT-767, LY-2562175 or Px-104.

[4] The pharmaceutical agent of any of [1]-[3] above, in which the FXR agonist is obeticholic acid or INT-767.

[5] The pharmaceutical agent of any of [1]-[4] above, in which the FXR agonist is obeticholic acid.

[6] The pharmaceutical agent of any of [1]-[4] above, in which the FXR agonist is INT-767.

[7] The pharmaceutical agent of any of [1]-[6] above, in which the ARB is losartan, candesartan, telmisartan, valsartan, olmesartan, irbesartan or azilsartan.

[8] The pharmaceutical agent of any of [1]-[7] above, in which the ARB is losartan.

[9] The pharmaceutical agent of any of [1]-[7] above, in which the ARB is candesartan.

[10] The pharmaceutical agent of any of [1]-[7] above, in which the ARB is telmisartan.

[11] The pharmaceutical agent of any of [1]-[7] above, in which the ARB is valsartan.

[12] The pharmaceutical agent of any of [1]-[7] above, in which the ARB is olmesartan.

[13] The pharmaceutical agent of any of [1]-[7] above, in which the ARB is irbesartan.

[14] The pharmaceutical agent of any of [1]-[7] above, in which the ARB is azilsartan.

[15] A therapeutic agent for non-alcoholic steatohepatitis (NASH), comprising the combination pharmaceutical agent of any of [1]-[14] above.

[16] The therapeutic agent of [15] above, characterized by combined use of a farnesoid X receptor agonist (FXR agonist) or a pharmaceutically acceptable salt thereof and an angiotensin II receptor blocker (ARB) or a pharmaceutically acceptable salt thereof.

[17] The therapeutic agent of [16] above, characterized in that the FXR agonist or a pharmaceutically acceptable salt thereof and the ARB or a pharmaceutically acceptable salt thereof are administered simultaneously or separately at different times.

[18] A therapeutic agent for non-alcoholic steatohepatitis (NASH) comprising a farnesoid X receptor agonist (FXR agonist) or a pharmaceutically acceptable salt thereof, characterized by combined use of an angiotensin II receptor blocker (ARB) or a pharmaceutically acceptable salt thereof.

[19] A therapeutic agent for non-alcoholic steatohepatitis (NASH) comprising an angiotensin II receptor blocker (ARB) or a pharmaceutically acceptable salt thereof, characterized by combined use of a farnesoid X receptor agonist (FXR agonist) or a pharmaceutically acceptable salt thereof.

[20] The therapeutic agent of [18] or [19] above, in which the FXR agonist is obeticholic acid, chenodeoxycholic acid, INT-767, LY-2562175, Px-104 or LJN-452.

[21] The therapeutic agent of any of [18]-[20] above, in which the FXR agonist is obeticholic acid, chenodeoxycholic acid, INT-767, LY-2562175 or Px-104.

[22] The therapeutic agent of any of [18]-[21] above, in which the FXR agonist is obeticholic acid or INT-767.

[23] The therapeutic agent of any of [18]-[22] above, in which the FXR agonist is obeticholic acid.

[24] The therapeutic agent of any of [18]-[22] above, in which the FXR agonist is INT-767.

[25] The therapeutic agent of any of [18]-[24] above, in which the ARB is losartan, candesartan, telmisartan, valsartan, olmesartan, irbesartan or azilsartan.

[26] The therapeutic agent of any of [18]-[25] above, in which the ARB is losartan.

[27] The therapeutic agent of any of [18]-[25] above, in which the ARB is candesartan.

[28] The therapeutic agent of any of [18]-[25] above, in which the ARB is telmisartan.

[29] The therapeutic agent of any of [18]-[25] above, in which the ARB is valsartan.

[30] The therapeutic agent of any of [18]-[25] above, in which the ARB is olmesartan.

[31] The therapeutic agent of any of [18]-[25] above, in which the ARB is irbesartan.

[32] The therapeutic agent of any of [18]-[25] above, in which the ARB is azilsartan.

[33] The therapeutic agent of any of [15]-[32] above, in which the above-mentioned NASH treatment is the inhibition of hepatic fibrosis in NASH.

[34] Use of the combination pharmaceutical agent of any of [1]-[14] above for producing a therapeutic agent for non-alcoholic steatohepatitis (NASH).

[35] Use of the combination pharmaceutical agent of any of [1]-[14] above for producing an agent for inhibiting hepatic fibrosis in NASH.

[36] A method for the treatment of non-alcoholic steatohepatitis (NASH), characterized in that a combination of a farnesoid X receptor agonist (FXR agonist) or a pharmaceutically acceptable salt thereof and an angiotensin II receptor blocker (ARB) or a pharmaceutically acceptable salt thereof is administered to a patient in a therapeutically effective dose.

[37] The treatment method of [36] above, in which the FXR agonist is obeticholic acid, chenodeoxycholic acid, INT-767, LY-2562175, Px-104 or LJN-452.

[38] The treatment method of [36] or [37] above, in which the FXR agonist is obeticholic acid, chenodeoxycholic acid, INT-767, LY-2562175 or Px-104.

[39] The treatment method of any of [36]-[38] above, in which the FXR agonist is obeticholic acid or INT-767.

[40] The treatment method of any of [36]-[39] above, in which the FXR agonist is obeticholic acid.

[41] The treatment method of any of [36]-[39] above, in which the FXR agonist is INT-767.

[42] The treatment method of any of [36]-[41] above, in which the ARB is losartan, candesartan, telmisartan, valsartan, olmesartan, irbesartan or azilsartan.

[43] The treatment method of any of [36]-[42] above, in which the ARB is losartan.

[44] The treatment method of any of [36]-[42] above, in which the ARB is candesartan.

[45] The treatment method of any of [36]-[42] above, in which the ARB is telmisartan.

[46] The treatment method of any of [36]-[42] above, in which the ARB is valsartan.

[47] The treatment method of any of [36]-[42] above, in which the ARB is olmesartan.

[48] The treatment method of any of [36]-[42] above, in which the ARB is irbesartan.

[49] The treatment method of any of [36]-[42] above, in which the ARB is azilsartan.

[50] The treatment method of any of [36]-[49] above, in which the above-mentioned NASH treatment is inhibition of hepatic fibrosis in NASH.

[51] A combination of a farnesoid X receptor agonist (FXR agonist) or a pharmaceutically acceptable salt thereof and an angiotensin II receptor blocker (ARB) or a pharmaceutically acceptable salt thereof for use in the treatment of non-alcoholic steatohepatitis (NASH).

[52] The combination of [51] above, in which the FXR agonist is obeticholic acid, chenodeoxycholic acid, INT-767, LY-2562175, Px-104 or LJN-452.

[53] The combination of [51] or [52] above, in which the FXR agonist is obeticholic acid, chenodeoxycholic acid, INT-767, LY-2562175 or Px-104.

[54] The combination of any of [51]-[53] above, in which the FXR agonist is obeticholic acid or INT-767.

[55] The combination of any of [51]-[54] above, in which the FXR agonist is obeticholic acid.

[56] The combination of any of [51]-[54] above, in which the FXR agonist is INT-767.

[57] The combination of any of [51]-[56] above, in which the ARB is losartan, candesartan, telmisartan, valsartan, olmesartan, irbesartan or azilsartan.

[58] The combination of any of [51]-[57] above, in which the ARB is losartan.

[59] The combination of any of [51]-[57] above, in which the ARB is candesartan.

[60] The combination of any of [51]-[57] above, in which the ARB is telmisartan.

[61] The combination of any of [51]-[57] above, in which the ARB is valsartan.

[62] The combination of any of [51]-[57] above, in which the ARB is olmesartan.

[63] The combination of any of [51]-[57] above, in which the ARB is irbesartan.

[64] The combination of any of [51]-[57] above, in which the ARB is azilsartan.

[65] The combination of any of [51]-[64] above, in which the above-mentioned NASH treatment is inhibition of hepatic fibrosis in NASH.

[66] A kit for the treatment of non-alcoholic steatohepatitis (NASH), comprising:
1) a pharmaceutical agent comprising a farnesoid X receptor agonist (FXR agonist) or a pharmaceutically acceptable salt thereof;
2) a pharmaceutical agent comprising an angiotensin II receptor blocker (ARB) or a pharmaceutically acceptable salt thereof; and
3) instructions for administration of a combination of 1) and 2) above.

[67] The kit of [66] above, in which the FXR agonist is obeticholic acid, chenodeoxycholic acid, INT-767, LY-2562175, Px-104 or LJN-452.

[68] The kit of [66] or [67] above, in which the FXR agonist is obeticholic acid, chenodeoxycholic acid, INT-767, LY-2562175 or Px-104.

[69] The kit of any of [66]-[68] above, in which the FXR agonist is obeticholic acid or INT-767.

[70] The kit of any of [66]-[69] above, in which the FXR agonist is obeticholic acid.

[71] The kit of any of [66]-[69] above, in which the FXR agonist is INT-767.

[72] The kit of any of [66]-[71] above, in which the ARB is losartan, candesartan, telmisartan, valsartan, olmesartan, irbesartan or azilsartan.

[73] The kit of any of [66]-[72] above, in which the ARB is losartan.

[74] The kit of any of [66]-[72] above, in which the ARB is candesartan.

[75] The kit of any of [66]-[72] above, in which the ARB is telmisartan.

[76] The kit of any of [66]-[72] above, in which the ARB is valsartan.

[77] The kit of any of [66]-[72] above, in which the ARB is olmesartan.

[78] The kit of any of [66]-[72] above, in which the ARB is irbesartan.

[79] The kit of any of [66]-[72] above, in which the ARB is azilsartan.

[80] The kit of any of [66]-[79] above, in which the above-mentioned NASH treatment is inhibition of hepatic fibrosis in NASH.

[81] An agent for inhibiting hepatic fibrosis in liver disease, comprising the combination pharmaceutical agent of any of [1]-[14] above.

[82] The agent for inhibiting hepatic fibrosis of [81] above, in which the liver disease is selected from hepatitis B; hepatitis C; parasitic liver disease; post-transplant bacterial infections, post-transplant viral infections, or post-transplant fungal infections; alcoholic liver disease (ALD); non-alcoholic fatty liver disease (NAFLD); methotrexate-induced liver disease, isoniazid-induced liver disease, oxyphenistatin-induced liver disease, methyldopa-induced liver disease, chlorpromazine-induced liver disease, tolbutamide-induced liver disease, or amiodarone-induced liver disease; autoimmune hepatitis; sarcoidosis; Wilson's disease; hemochromatosis; Gaucher's disease; glycogen storage disease type III, glycogen storage disease type IV, glycogen storage disease type VI, glycogen storage disease type IX, or glycogen storage disease type X; $\alpha$-1 antitrypsin deficiency; Zellweger syndrome; tyrosinemia; levulosemia; galactosemia; Budd-Chiari syndrome-related angiopathy, venoocclusive disease-related angiopathy, portal vein thrombosis-related angiopathy; or congenital hepatic fibrosis.

[83] The agent for inhibiting hepatic fibrosis of [81] or [82] above, in which the liver disease is either ALD or NAFLD.

[84] The agent for inhibiting hepatic fibrosis of any of [81]-[83] above, in which the liver disease is NAFLD.

Effect of the Invention

According to the present invention, it can be expected that by administering a combination or mixture of an FXR agonist or a pharmaceutically acceptable salt thereof, particularly obeticholic acid or a pharmaceutically acceptable salt thereof, with an ARB or a pharmaceutically acceptable salt thereof, it will become possible to achieve a dramatic increase in therapeutic effect compared to monotherapy with either of these drugs, thus providing an effect of treating and/or preventing NASH, more particularly an effect of preventing, inhibiting, and/or alleviating hepatic fibrosis in NASH. Moreover, according to the present invention, it can be expected that by increasing the therapeutic effect using the two above-mentioned drugs (the active ingredients) in combined or mixed administration, it will become possible to administer these drugs in a decreased dosage compared to their dosage in monotherapy, thus reducing adverse reactions associated therewith.

Moreover, the present invention can be expected to show a therapeutic effect on hepatic fibrosis not only in NASH, but in all types of liver disease, including hepatitis B; hepatitis C; parasitic liver disease; post-transplant bacterial infections, post-transplant viral infections, and post-transplant fungal infections; alcoholic liver disease (ALD); non-alcoholic fatty liver disease (NAFLD); methotrexate-induced liver disease, isoniazid-induced liver disease, oxyphenistatin-induced liver disease, methyldopa-induced liver disease, chlorpromazine-induced liver disease, tolbutamide-induced liver disease, or amiodarone-induced liver disease; autoimmune hepatitis; sarcoidosis; Wilson's disease; hemochromatosis; Gaucher's disease; glycogen storage disease type III, glycogen storage disease type IV, glycogen storage disease type VI, glycogen storage disease type IX, and glycogen storage disease type X; α-1 antitrypsin deficiency; Zellweger syndrome; tyrosinemia; levulosemia; galactosemia; Budd-Chiari syndrome-related angiopathy, veno-occlusive disease-related angiopathy, and portal vein thrombosis-related angiopathy; and congenital hepatic fibrosis.

SIMPLIFIED EXPLANATION OF THE FIGURES

FIG. 1 shows representative examples of micrographs of Sirius Red-stained liver sections of the groups (G1-G5) of working example 1.

FIG. 2 shows the results of a semiquantitative analysis of the histological characteristics of the progression of fibrosis in the groups of working example 1. In the figure, moreover, the bars indicate the average area index of the fibrotic areas in the various groups. Asterisks (**) indicate statistically significant differences among the groups shown ($p<0.01$, Student's t-test).

FIG. 3 shows representative examples of micrographs of α-smooth muscle actin (α-SMA) immunohistologically stained liver sections of the groups (G1-G5) in working example 2.

FIG. 4 shows the results of a semiquantitative analysis of the immunohistochemical characteristics of the various groups of working example 2. In the figure, moreover, the bars indicate the average area index of the α-SMA stained areas in the various groups. Asterisks (**) indicate statistically significant differences among the groups shown ($p<0.01$; Student's t-test).

FIG. 5 shows the results of a quantitative analysis by RT-PCR of TGIF-β1 and α1(I) procollagen mRNA expression in the groups of working example 2. In the figure, moreover, the bars indicate the amount of mRNA expression. Asterisks (*; **) indicate statistically significant differences among the groups shown (*: $p<0.05$; **: $p<0.01$).

FIG. 6 shows the results of a study of the effect of inhibiting the proliferation capacity of human hepatic stellate cells in the groups of working example 3 (G1, G2L, G2A, G2AL, G3, G4, G5) when losartan was used as an ARB.

FIG. 7 shows the results of a study of the effect of inhibiting the proliferation capacity of human hepatic stellate cells in the groups of working example 3 (G1, G2AL, G3, G4, G5) when valsartan was used as an ARB.

FIG. 8 shows the results of a study of the effect of inhibiting the proliferation capacity of human hepatic stellate cells in the groups of working example 3 (G1, G2AL, G3, G4, G5) when candesartan was used as an ARB.

FIG. 9 shows the results of a study of the effect of inhibiting TGF-β1 fibrosis marker gene expression in the groups of working example 3 (G1, G2L, G2A, G2AL, G3, G4, G5) when losartan was used as an ARB.

FIG. 10 shows the results of a study of the effect of inhibiting TGF-β1 fibrosis marker gene expression in the groups of working example 3 (G1, G2AL, G3, G4, G5) when valsartan was used as an ARB.

FIG. 11 shows the results of a study of the effect of inhibiting TGF-β1 fibrosis marker gene expression in the groups of working example 3 (G1, G2AL, G3, G4, G5) when candesartan was used as an ARB.

FIG. 12 shows the results of a study of the effect of inhibiting α1(I) procollagen fibrosis marker gene expression in the groups of working example 3 (G1, G2L, G2A, G2AL, G3, G4, G5) when losartan was used as an ARB.

FIG. 13 shows the results of a study of the effect of inhibiting α1(I) procollagen fibrosis marker gene expression in the groups of working example 3 (G1, G2AL, G3, G4, G5) when valsartan was used as an ARB.

FIG. 14 shows the results of a study of the effect of inhibiting α1(I) procollagen fibrosis marker gene expression in the groups of working example 3 (G1, G2AL, G3, G4, G5) when candesartan was used as an ARB.

FIG. 15 shows the results of a study of the effect of alleviating liver cell swelling in the drug administration groups of working example 7 (G3, G4, G5). In the figure, moreover, the bars indicate the liver cell swelling improvement rate.

FIG. 16 shows the results of a study of the effect of improving ALT activity in the drug administration groups of working example 8 (G3, G4, G5). In the figure, moreover, the bars indicate the change in ALT activity.

DESCRIPTION OF THE PREFERRED EMBODIMENTS

In the context of the present invention, the term "farnesoid X receptor agonist" or "FXR agonist" refers to ligands specific for the farnesoid X receptor (FXR), which are compounds having the action of binding to FXR, thus specifically stimulating ligand-dependent FXR transcriptional activity (as differentiated from the baseline level determined in the absence of any ligand) (said compounds include natural compounds, semisynthetic compounds derived from natural compounds, and synthetic compounds). This action is also simply referred to as an FXR-stimulating action or an FXR-activating action. Moreover, as synonyms for "FXR agonist," "FXR activator," "FXR stimulator," "FXR-activating ligand." "TAR-specific ligand," or simply "FXR ligand" may also be used.

FXRs (farnesoid X receptors), which are nuclear receptors having bile acids as ligands, are known to be involved in bile acid metabolism, cholesterol metabolism, lipid metabolism, etc., and FXR agonists are expected to have an effect on disorders such as liver disease, metabolic diseases, and organ fibrosis.

The natural bile acid chenodeoxycholic acid was isolated as the natural FXR ligand having the highest activity, and oheticholic acid was subsequently found to have the strongest FXR-stimulating action among the semi synthetic alkylated bile acids.

There are no particular limitations on the FXR agonist, with examples including the oheticholic acid, chenodeoxycholic acid, INT-767, LY-2562175, Px-104, LJN-452 shown in the following table. The FXR agonist used in the present invention is preferably obeticholic acid or INT-767, and more preferably obeticholic acid.

The FXR agonist used in the present invention may also include two or more FXR agonists.

TABLE 1

| Drug name | Structural formula | [CAS no.] and/or Reference |
|---|---|---|
| Obeticholic acid (INT-747 or DSP-1747) | | [459789-99-2] WO2002/072598 |
| Chenodeoxycholic acid | | [474-25-9] |
| INT-767 | | WO2008/002573 |
| LY-2562175 | | WO2009/012125 |

TABLE 1-continued

| Drug name | Structural formula | [CAS no.] and/or Reference |
|---|---|---|
| Px-104 | 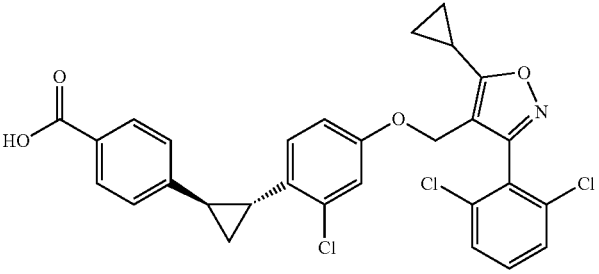 [SMILES: O=C(O)c1ccc([C@@H]2C[C@H]2c2ccc(OCc3c(-c4c(Cl)cccc4Cl)noc3C3CC3)cc2Cl)cc1] | [1268244-88-7]<br>WO2011/020615 |

The FXR agonist, more particularly any of the above-mentioned compounds, may be any commonly-known compound and may be produced by any commonly-known method. For example, obeticholic acid may be produced by the method disclosed in Japanese Examined Patent Application Publication No. 2015-52162.

There are no particular limitations on the "angiotensin II receptor blocker" or "ARB" used in the invention, with examples including the drugs mentioned in the table below, such as losartan, candesartan, telmisartan, valsartan, olmesartan, irbesartan, and azilsartan. The ARB used in the present invention is preferably losartan, valsartan or irbesartan, more preferably losartan or irbesartan, and most preferably losartan.

In another embodiment, the drug used is preferably candesartan, telmisartan, olmesartan or azilsartan, more preferably telmisartan, olmesartan or azilsartan, even more preferably telmisartan or olmesartan, and most preferably olmesartan.

Moreover, in another embodiment, the drug used is preferably candesartan, telmisartan or azilsartan, more preferably telmisartan or azilsartan, and most preferably telmisartan. In a further embodiment, the drug used is preferably candesartan, olmesartan or azilsartan, more preferably olmesartan or azilsartan, and most preferably azilsartan. In a further embodiment, the drug used is preferably candesartan, telmisartan or olmesartan, more preferably candesartan or olmesartan, and most preferably candesartan. In a further embodiment, the drug used is preferably losartan, valsartan or candesartan.

The ARB of the present invention may be included in the form of two or more ARBs.

In the context of the present invention, the term "losartan" refers both to losartan having the structural formula shown in the table below and to the commercially-used potassium salt of losartan (losartan potassium). Losartan potassium is preferred.

In the context of the present invention, the term "candesartan" refers both to candesartan having the structural formula shown in the table below and to the commercially used cilexitil ester of candesartan (candesartan cilexitil). Candesartan cilexitil is preferred.

In the context of the present invention, the term "olmesartan" refers both to olmesartan having the structural formula shown in the table below and to the tnedoxomil ester of olmesartan (olmesartan medoxomil). Olmesartan medoxomil is preferred.

TABLE 2

| Drug name | Structural formula |
|---|---|
| Losartan | 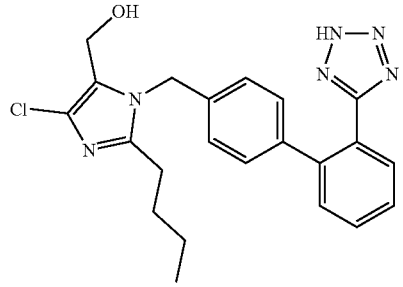 [SMILES: CCCCc1nc(Cl)c(CO)n1Cc1ccc(-c2ccccc2-c2nn[nH]n2)cc1] |
| Losartan potassium | 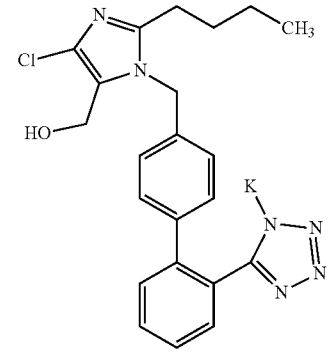 |
| Candesartan | 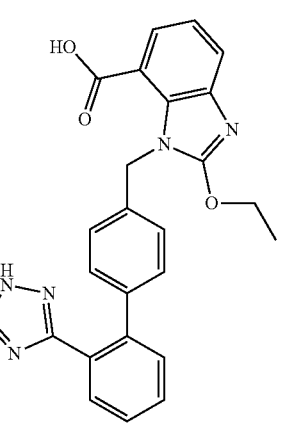 |

TABLE 2-continued

| Drug name | Structural formula |
|---|---|
| Candesartan cilexitil | *(structure shown) and enantiomers* |
| Telmisartan | *(structure shown)* |
| Valsartan | *(structure shown)* |
| Olmesartan | *(structure shown)* |
| Olmesartan medoxomil | *(structure shown)* |
| Irbesartan | *(structure shown)* |
| Azilsartan | *(structure shown)* |

The ARB or a pharmaceutically acceptable salt thereof may be produced by a commonly-known method. A commercial ARB may also be used.

The FXR agonist and ARB of the present invention may be used in the form of a pharmaceutically acceptable salt. The "pharmaceutically acceptable salt" may be any pharmaceutically acceptable salt that does not affect the activity of the FXR agonist or ARB itself, with examples including salts of inorganic acids, salts of organic acids, salts of inorganic salts, and salts of organic salts.

In cases where the pharmaceutical agents are basic compounds, examples of suitable salts include acid addition salts with inorganic acids (such as hydrochloric acid, hydrobromic acid, hydroiodic acid, sulfuric acid, nitric acid, or phosphoric acid) or organic acids (such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, or glutamic acid).

In cases where the pharmaceutical agents are acidic compounds, examples of suitable salts include base addition salts with inorganic salts (such as sodium salt, potassium salt, lithium salt, barium salt, calcium salt, or magnesium salt) or organic salts (such as pyridinium salt, picolinium salt, or triethylammonium salt).

In the context of the present invention, the term "pharmaceutically acceptable salt" includes hydrates and solvates. Examples of the solvents used to form such substances include water and physiologically acceptable organic solvents such as ethanol and acetone, but there are no particular limitations in this respect.

In the case of use of combinations of multiple FXR agonists and/or ARBs, the salts and solvates of the various compounds used may be the same or different.

In the context of the present invention, the term "pharmaceutically acceptable" refers to the properties of compounds, substances, compositions, carriers, and/or dosage forms which, within the scope of sound medical judgment, do not cause any excessive toxicity, irritation, allergic response, or other problems or adverse events, show a reasonable risk-to-benefit ratio, and are appropriate for use in contact with human and animal tissue.

Moreover, prodrugs of FXR agonists and ARBs or pharmaceutically acceptable salts thereof are also included in the scope of the present invention. In the context of the invention, the term "prodrug" refers to chemically-modified functional derivatives of the compounds of the present invention that manifest their pharmacological effects after being converted into phartncologically active compounds in the body or after reaching the target site.

There are no particular limitations on the prodrugs used in the present invention, with examples including the following types:

(1) A phosphoric ester prodrug of a hydroxyl or amino group of the compound according to the invention;

(2) a carbonate or carbamate prodrug of a hydroxyl or amino group of the compound according to the invention;

(3) an amino prodrug of a carboxylic acid or amino group of the compound according to the invention;

(4) an amino acid-linked prodrug of a carboxylic acid or amino group of the compound according to the invention; and (5) an oxime prodrug of a ketone, amidine, or guanidine of the compound according to the invention.

For example, the prodrug of the present invention may be produced by the methods described in Nature Reviews Drug Discovery 7; 255-270 (2008); or Journal of Medicinal Chemistry 2005, 48 (16), 5305-5320.

Moreover, the FXR agonist according to the present invention may be used in the form of an amino acid conjugate. In the context of the present specification, the term "amino acid conjugate" refers to any desired suitable amino acid conjugate with a compound (such as obeticholic acid or chenodeoxycholic acid).

Most natural bile acids are present in the body in the form of amino acid conjugates biosynthesized by conjugation, chiefly with amino acids such as glycine and taurine (also referred to as conjugated bile acids). In humans, for example, cholic acid is conjugated with glycine and taurine to form the conjugated bile acids glycocholic acid and taurocholic acid respectively.

In the same manner, for example, the FXR agonists of the present invention form amino acid conjugates with the natural bile acid chenodeoxycholic acid and the semisynthetic alkylated bile acid obeticholic acid. Such amino acid conjugate compounds should preferably have the additional advantage of showing increased stability in the bile or intestinal fluid. Any suitable amino acids preferably include glycine and taurine, but there are no particular limitations in this respect. More particularly, obeticholic acid may be used in the form of an amino acid conjugate, with said amino acid conjugate including glycine and taurine conjugates.

The "non-alcoholic steatohepatitis (NASH) therapeutic agent" of the present invention is an agent for treatment and/or prevention in patients diagnosed with NASH or suspected of having NASH. According to standards such as the NASH/NAFLD Practice Guideline of the Japan Society of Hepatology, non-alcoholic fatty liver disease (NAFLD) is a superordinate concept that includes NASH, with NAFLD constituting a pathology determined by histological or image diagnosis of fatty liver, excluding other liver diseases such as alcoholic liver injury. Fatty liver disease is a general term for diseases including liver damage caused by the deposition of neutral fats (TGs) in the hepatocytes. As many cases of NAFLD result from disorders such as obesity, diabetes, dyslipidernia, and hypertension, they are treated as hepatic lesions associated with metabolic syndrome. Histologically, NAFLD is based on large-droplet hepatic steatosis, and this disease is divided into the two classifications of non-alcoholic fatty liver disease (NAFL) and NASH. In NAFL, also referred to as simple fatty liver, the prognosis is considered favorable, with virtually no progression. NASH is characterized by fat accumulation, inflammation, and liver cell injury (ballooning), and with increasing severity, NASH is accompanied by progressive hepatic fibrosis. The prognosis of NASH is considered to depend on how far hepatic fibrosis has progressed, and in cases with a poor prognosis, the disease may progress to liver cirrhosis and liver cell carcinoma.

The "agent for treating NASH" of the present invention is capable of preventing and/or treating NAFLD, as well as preventing the progression from NAFL to NASH.

The "agent for inhibiting hepatic fibrosis" of the present specification is an agent for preventing, inhibiting, and/or alleviating hepatic fibrosis. In the context of the present invention, the term "fibrogenesis" includes the pathological state of fibrosis and the transition thereto, as well as the occurrence, progression, and aggravation thereof. "Fibrosis" refers to conditions including the accumulation of excess fibrous tissue in the tissues or organs (such as scar tissue). Such scar tissue can occur as a result of factors such as disease, trauma, or chemical toxicity, or in response to infection, inflammation, or injury to the organs. Fibrosis can occur in a variety of tissues and organs (such as the liver, kidneys, intestines, lungs, and heart).

In the context of the present invention, the term "hepatic fibrosis" refers to tissue fibrosis occurring in the liver, and includes the pathological state of fibrosis and the transition thereto, as well as the occurrence, progression, and aggravation thereof.

Moreover, the present invention is not particularly limited to various stages of hepatic fibrosis, but relates to all types of liver disease, including hepatitis B; hepatitis C; parasitic liver disease; post-transplant bacterial infections, post-transplant viral infections, or post-transplant fungal infections; alcoholic liver disease (ALD); non-alcoholic fatty liver disease (NAFLD), including non-alcoholic steatohepatitis (NASH); methotrexate-induced liver disease, isoniazid-induced liver disease, oxyphenistatin-induced liver disease, methyldopa-induced liver disease, chlorpromazine-induced liver disease, tolbutamide-induced liver disease, or amiodarone-induced liver disease; autoimmune hepatitis; sarcoidosis; Wilson's disease; hemochromatosis; Gaucher's disease; glycogen storage disease type III, glycogen storage disease type IV, glycogen storage disease type VI, glycogen storage disease type IX, or glycogen storage disease type X; α-1 antitrypsin deficiency; Zellweger syndrome; tyrosinemia; levulosemia; galactosemia; Budd-Chiari syndrome-related angiopathy, veno-occlusive disease-related angiopathy, or portal vein thrombosis-related angiopathy; or congenital hepatic fibrosis, and the invention can be expected to be effective in the treatment of hepatic fibrosis in all of these diseases.

The present invention can preferably be used in hepatic fibrosis associated with alcoholic liver disease (ALD) or non-alcoholic fatty liver disease (NAFLD) (including non-alcoholic steatohepatitis (NASH)), more preferably in hepatic fibrosis associated with NAFLD (including NASH), and particularly preferably in hepatic fibrosis associated with NASH.

Moreover, the present invention can show an outstanding therapeutic effect in patients with NASH secondary to metabolic disorders such as obesity and type 2 diabetes mellitus (T2DM). The present invention is particularly suitable for use in the treatment of NASH caused by metabolic diseases. It is also suitable for use in the treatment of NASH accompanied by hypertension.

The term "treatment" includes all treatment concerning a disease and its symptoms (such as improvement, alleviation, and inhibition of progression). This may also include prevention of the symptoms and/or progression of the disease. Moreover, the terms "treatment" or "treating" include any effects that produce an improvement in any disease state (such as reducing, decreasing, inhibiting the progression of, alleviating, preventing, regulating, or eliminating the disease). For example, "treatment" of or "treating" a disease state includes preventing the disease state, specifically stopping the progression of the disease state or its clinical symptoms, or alleviating the disease state, specifically temporarily or permanently, or partially or completely, and eliminating the disease state or its clinical symptoms.

In the context of the present invention, "treatment" refers to the treatment and/or prevention of NASH in a patient, such as a mammal or in particular a human, and to the prevention, inhibition, and/or alleviation of hepatic fibrosis. For example, treatment of NASH includes prevention of the occurrence of NASH, inhibition of the progression of NASH, treatment of NASH, inhibition of recurrence following treatment of NASH, etc. This also includes the prevention and/or treatment of NAFLD and the prevention of progression from NAFL to NASH.

"Patient" refers to humans and other animals, such as dogs, cats, and mice. Mammals are preferred, and among these, humans are particularly preferred.

The term "therapeutically effective dose" refers to the dose of a drug or pharmaceutical agent that elicits the biological or pharmaceutical response desired by the researcher or physician in a tissue, system, animal, or human. Moreover, in the case of administration to a mammal for the treatment of a disease, the "therapeutically effective dose" refers to the dose of a drug (an FXR agonist, ARB, etc.) sufficient to treat the disease. The "therapeutically effective dose" will vary depending on the drug, the disease, and severity thereof, and in the case of a mammal, the age, body weight, etc. thereof.

Moreover, the term "effective dose" also refers to the dose of a drug (an FXR agonist, ARB, etc.) that produces an acute or chronic therapeutic effect in administration of the proper dose. Examples of this therapeutic effect include the prevention, correction, blocking, or reversal to a detectable extent of the signs, symptoms, and underlying pathology of a disease/pathological state (such as hepatic fibrosis) and complications related thereto.

Examples of this effective dose are the dose of the FXR agonist or ARB of the present invention in monotherapy, the combined dose of the FXR agonist and the ARB of the present invention, and/or the dose of the combination pharmaceutical agent of the present invention together with another NASH therapeutic agent.

In the present invention, there are no particular limitations on the ratio of the combination of an FXR agonist or a pharmaceutically acceptable salt thereof and an ARB or a pharmaceutically acceptable salt thereof, and this ratio may be selected as appropriate so as to achieve the desired effect of preventing and/or treating NASH. There are no particular limitations on this combination ratio, and it may be selected as appropriate, for example in the ranges of 1:100-100:1, 1:10-10:1, or 1:3-3:1.

In the combination of an FXR agonist or a pharmaceutically acceptable salt thereof and an ARB or a pharmaceutically acceptable salt thereof of the present invention, the two agents may be administered separately, or they may be administered together as a single dosage form. Moreover, one of the components of the combination of the invention may be administered prior to, simultaneously with, or after the other component. The components may be prepared as pharmaceutical formulations in the form of a single dosage or separate dosages.

There are no particular limitations on the embodiments of the combination of an FXR agonist or a pharmaceutically acceptable salt thereof and an ARB or a pharmaceutically acceptable salt thereof according to the invention, and embodiments (I) and (II) below can be mentioned as examples:

(I) an embodiment containing the two components of an FXR agonist or a pharmaceutically acceptable salt thereof and an ARB or a pharmaceutically acceptable salt thereof (single pharmaceutical agent composition, mixed formulation) as a single formulation; and (II) an embodiment containing an FXR agonist or a pharmaceutically acceptable salt thereof (pharmaceutical composition) and an ARB or a pharmaceutically acceptable salt thereof (pharmaceutical composition) as separate formulations.

In the case of embodiment (II) above, the formulations can be administered simultaneously or separately at a suitable time interval, and a suitable administration schedule can be used in order to achieve the desired effect of preventing and/or treating NASH. Moreover, in the case of embodiment (II) above, the two formulations can be provided as a kit containing said formulations combined into a single package.

There are no particular limitations on the administration route of the present invention, with examples including oral, sublingual, buccal, parenteral (such as subcutaneous, intramuscular, or intravenous), rectal, topical, and intranasal administration. Oral or parental administration is preferred, with oral administration being particularly preferred. In the case of embodiment (II) above, one of the formulations can be administered orally and the other parenterally.

Examples of oral administration forms include tablets, capsules, granules, powders, and syrups. Examples of parenteral administration forms include injections, suppositories, inhalation preparations, transdermal absorption preparations, topical cutaneous preparations, eyedrops, and nose drops.

The active ingredients of the present invention may be formulated either individually or together in a preparation containing a common non-toxic pharmaceutically acceptable carrier, auxiliary, or vehicle suitable for the administration route in question. Among these administration forms, oral administration forms are preferred, with tablets, capsules, granules, powders, and syrups being particularly preferred. The above-mentioned oral and parenteral administration forms may be produced using commonly-known formulation additives, based for example on the methods specified in standards such as the General Regulations for Preparations of the 16th Revised Japanese Pharmacopoeia.

The pharmaceutical agent of the present invention may further contain pharmaceutically acceptable carriers, excipients, binders, stabilizers, and other components. For example, if the pharmaceutical dosage form of the present invention is an injection preparation, acceptable buffers, solubilizing agents, isotonising agents, and pH-adjusting agents may be added. Pharmaceutically acceptable components are known to the person skilled in the art, and they may be selected as appropriate within the scope of implementation by the person skilled in the art from the components specified, for example, in other written standards of the 16th Revised Japanese Pharmacopoeia.

There are no particular limitations on the dosage of the combination of active ingredients according to the present invention (an FXR agonist or a pharmaceutically acceptable salt thereof and an ARB or a pharmaceutically acceptable salt thereof), and it may be increased or decreased as appropriate depending on various conditions such as the patient's age, body weight, symptoms, and the form and frequency of administration. Moreover, the dosage of one of the components of the combination according to the present invention may be increased or decreased as appropriate independently of the other component.

Moreover, because of the increased therapeutic effect of administration of a combined or mixed preparation of the combination of active ingredients of the present invention (as two pharmaceutical agents, an FXR agonist or a pharmaceutically acceptable salt thereof and an ARB or a pharmaceutically acceptable salt thereof), it becomes possible to decrease the dosage (or the administered dosage) to lower than would be used in individual administration of the components, and as a result, a reduction in the adverse effects of said components can be expected. For example, FXR agonists (such as obeticholic acid) produce adverse effects such as pruritis, and by administering the combination of obeticholic acid and an ARB of the present invention in a combined or mixed preparation, for example, it becomes possible to use a dose that is lower than that required in monotherapy, thus allowing the frequency and/or severity of the adverse event of pruritis, for example, to be reduced.

The FXR agonist or a pharmaceutically acceptable salt thereof may be used in a daily dose of 0.1 mg-1 g, and preferably 1 mg-500 mg. For example, if the FXR agonist is obeticholic acid, the drug is used in adults in a daily dose of the free drug of 0.1 mg-1 g, preferably 1 mg-500 mg, more preferably 2 mg-100 mg, and particularly preferably 5 mg-50 mg, with administration of 1 mg, 2 mg, 2.5 mg, 5 mg, 10 mg, 12.5 mg, 20 mg, 25 mg, 40 mg, 50 mg or 10 mg being preferred.

Moreover, for example, if the FXR antagonist is INT-767, the drug is used in adults in a daily dose of the free drug of 0.1 mg-1 g, preferably 1 mg-500 mg, more preferably 2 mg-100 mg, and particularly preferably 5 mg-50 mg, with administration of 1 mg, 2 mg, 2.5 mg, 5 mg, 10 mg, 12.5 mg, 20 mg, 25 mg, 40 mg, 50 mg or 100 mg being preferred.

The ARB or a pharmaceutically acceptable salt thereof may be used in a daily dose of 0.1 mg-200 mg, and preferably 1 mg-100 mg. For example, if the ARB is losartan, or more particularly losartan potassium, the drug is used in adults in a daily dose of 1 mg-100 mg, preferably 2 mg-100 mg, more preferably 5 mg-100 mg, and particularly preferably 10 mg-50 mg, with administration of 1 mg, 2 mg, 2.5 mg, 5 mg, 10 mg, 12.5 mg, 20 mg, 25 mg, 40 mg, 50 mg or 100 mg being preferred.

Moreover, for example, if the ARB is irbesartan, the drug is used in adults in a daily dose of 1 mg-200 mg, preferably 2 mg-200 mg, more preferably 5 mg-200 mg, and particularly preferably 10 mg-100 mg, with administration of 1 mg, 2 mg, 2.5 mg, 5 mg, 10 mg, 12.5 mg, 20 mg, 25 mg, 40 mg, 50 mg, 100 mg or 200 mg being preferred.

Moreover, for example, if the ARB is olmesartan, or more particularly olmesartan medoxomil, the drug is used in adults in a daily dose of 1 mg-40 mg, preferably 2 mg-40 mg, more preferably 5 mg-40 mg, and particularly preferably 10 mg-20 mg, with administration of 1 mg, 2 mg, 2.5 mg, 5 mg, 10 mg, 12.5 mg, 20 mg, 25 mg or 40 mg being preferred.

Moreover, for example, if the ARB is telmisartan, the drug is used in adults in a daily dose of 1 mg-80 mg, preferably 2 mg-80 mg, more preferably 5 mg-80 mg, and particularly preferably 10 mg-40 mg, with administration of 1 mg, 2 mg, 2.5 mg, 5 mg, 10 mg, 12.5 mg, 20 mg, 25 mg, 40 mg, 50 mg or 80 mg being preferred.

Moreover, for example, if the ARB is candesartan, or more particularly candesartan cilexitil, the drug is used in adults in a daily dose of 0.2 mg-12 mg, preferably 0.5 mg-12 mg, more preferably 1 mg-12 mg, and particularly preferably 2 mg-8 mg, with administration of 0.2 mg, 0.5 mg, 1 mg, 2 mg, 2.5 mg, 4 mg, 5 mg, 8 mg, 10 mg or 12 mg being preferred.

Moreover, for example, if the ARB is valsartan, the drug is used in adults in a daily dose of 1 mg-160 mg, preferably 2 mg-160 mg, more preferably 5 mg-160 mg, and particularly preferably 10 mg-80 mg, with administration of 1 mg, 2 mg, 2.5 mg, 5 mg, 10 mg, 12.5 mg, 20 mg, 25 mg, 40 mg, 50 mg, 80 mg or 160 mg being preferred.

Moreover, for example, if the ARB is azilsartan, the drug is used in adults in a daily dose of 1 mg-40 mg, preferably 2 mg-40 mg, more preferably 5 mg-40 mg, and particularly preferably 10 mg-20 mg, with administration of 1 mg, 2 mg, 2.5 mg, 5 mg, 10 mg, 12.5 mg, 20 mg, 25 mg or 40 mg being preferred.

With respect to the administration interval, the above-mentioned dosages may be administered once daily or in divided doses 2 to several times daily.

There are no particular limitations on the preparation of these active ingredients in a single formulation, and for example, they may be mixed at a ratio of 0.01-100 parts by weight, preferably 0.1-10 parts by weight, and more preferably 0.3-3 parts by weight of the ARB or a pharmaceutically acceptable salt thereof per 1 part by weight of the FXR agonist or a pharmaceutically acceptable salt thereof. There are also no particular limitations with respect to single formulations, and for example, the total amount of active ingredients may account for 0.1-70% by weight of the pharmaceutical composition.

WORKING EXAMPLES

The following is an explanation of the present invention in further detail by means of working examples, but the scope of the invention is by no means limited by these examples.

Working Example 1

Method

As a rat NASH model, Otsuka Long-Evans Tokushima. Fatty (OLETF) rats, which are known as a model for naturally-occurring type II diabetes with obesity, were administered porcine serum (PS) in order to experimentally induce liver fibrosis, and the therapeutic effects of distilled water (vehicle administration group), obeticholic acid (an FXR agonist) and losartan (an ARB) (administration groups, combined administration group) were investigated according to the following method.

Animals Used

Male OLETF rats (n=40) and Long-Evans Tokushima Otsuka (LETO) rats=10; non-diabetic negative control group)

Drugs Used

Obeticholic acid (obtained from Intercept Pharmaceuticals, Inc. via Sumitomo Dainippon Pharma Co., Ltd.) was used as an FXR agonist, and commercial losartan (potassium salt of losartan; referred to in this working example simply as "losartan") was used as an ARB.

Administered Dosage, Administration Period

Obeticholic acid (30 mg/kg/day) and/or losartan (30 mg/kg/day) was/were given by forced oral administration; the administration period was 8 weeks in all cases.

Experimental Method 12-week-old OLETF rats were randomly divided into 4 groups (G2, G3, G4, G5) (n=10 for each group) and given intraperitoneal administrations of 1.0 ml/kg of porcine serum (PS) twice weekly for 8 weeks. 12-week-old LETO rats (n=10) were taken as group G1 and administered PS in the same manner. On the same day on which PS administration was begun, the group G3 and G4 rats were respectively administered obeticholic acid (30 mg/kg/day) and losartan (30 mg/kg/day) daily for 8 weeks by forced continuous oral administration. The group G5 rats were given daily combined administration of obeticholic acid (30 mg/kg/day) and losartan (30 mg/kg/day) for 8 weeks in the same manner. The rats in the G1 group (LETO) and G2 group (OLETF) were administered distilled water as a vehicle instead of the drugs and taken as the negative and positive control group respectively (with the same administration method as in the drug groups).

Histological Analysis

In order to evaluate the progression of hepatic fibrosis, formalin-fixed paraffin-embedded liver sections (5 μm in width) were taken from rats that had completed the above testing and stained with Sirius Red. Micrographs of the stained sections were taken and collected (in all of the rats, microscopic images were collected with a total of 10 fields per sample), and the micrographs of the various groups were compared. In order to quantitate the progression of fibrosis in the various groups, a semiquantitative analysis of the histological characteristics of the images of the stained specimens collected was conducted using ImageJ software from the NIH (National Institutes of Health).

Results

The results of drug administration in the rat NASH model are shown in FIG. 1 and FIG. 2.

FIG. 1 shows representative examples of micrographs of Sirius Red-stained liver sections of the various groups. Comparison of the negative control group (G1) and positive control group (G2) showed that administration of PS caused no progression of hepatic fibrosis in the LETO rats (G1), with marked progression of hepatic fibrosis being observed in the OLETF rats (G2) only. Moreover, fibrosis was moderately inhibited in the obeticholic acid monotherapy group (G3) and losartan monotherapy group (G4), although one would have expected these groups to show the same marked progression as in the positive control group (G2) administered the vehicle alone, and surprisingly, the group given combined administration of both obeticholic acid and losartan (G5) showed complete inhibition of hepatic fibrosis to the same extent as the negative control group (G1). This effect in the combined administration group (G5) was extremely pronounced compared to the respective monotherapy groups (G3, G4), and this can be said to constitute an unanticipated synergistic effect.

FIG. 2 shows the results of a semiquantitative analysis of the histological characteristics of the progression of fibrosis in the various groups. The fibrosis index (FI) shown on the vertical axis of the figure is the average area index of the fibrotic areas as calculated by computer analysis of the stained liver section images taken and collected from the rats in the various groups. This result quantitatively supports the results for histological characteristics seen in the micrographs of FIG. 1

FI values showed statistically significant differences among the various groups ($p<0.01$; Student's t-test). The positive control group (G2) showed extremely high FI values that were approximately 20 times greater than in the negative control group (G1). The obeticholic acid (G3) and losartan (G4) monotherapy groups showed moderate but significant decreases, with respective decreases to approximately $6/10$ and $7/10$ of the levels in the positive control group. Moreover, the values in the group given combined administration of both obeticholic acid and losartan (G5) were approximately $1/20$ of the level in the positive control group, with the FI values showing a significant and marked decrease to the same level as in the negative control group (G1). This result shows in a quantitatively and statistically significant manner that combined administration completely inhibits hepatic fibrosis, showing a highly pronounced synergistic effect compared to monotherapy with the respective drugs.

Working Example 2

Using the liver sections from the rats in the various groups obtained in working example 1, an immunohistochemical study by immunohistological staining with α-smooth muscle actin (α-SMA) antibody and a quantitative analysis of transforming growth factor-β1 TGF-β1) and collagen (α1(I) procollagen) mRNA expression were conducted. α-SMA is known to be an indicator (marker) of activation of hepatic stellate cells (HSCs) (also known as hepatic star cells). Moreover, activation of hepatic stellate cells (HSC), overproduction of TGF-β1 (a fibrosis-promoting cytokine) accompanying said activation, and overproduction of extracellular matrix components such as collagen are thought to play a central role in the mechanism of progressive hepatic fibrosis in NASH. For this reason, mRNA expression of TGF-β1 and collagen (α1(I) procollagen) can be a fibrosis indicator (marker).

(1) Immunohistochemical Study by Immunohistological Staining with α-SMA Antibody Method Using the same method as described under [Histological analysis] in working example 1 above, except that immunohistological staining with α-SMA antibody was used instead of Sirius Red staining, a comparison of the micrographs among the various groups and a semiquantitative analysis of the immunohistochemical characteristics of the collected stained section images were carried out, and the blocking effect of obeticholic acid and losartan (administration groups, combined administration group) on HSC activation in the progression of hepatic fibrosis was evaluated.

Results

The results are shown in FIG. 3 and FIG. 4.

FIG. 3 shows representative examples of micrographs of α-SMA immunohistologically stained sections in the various groups. As was the case for the histological analysis results of working example 1 (i.e., inhibition of hepatic fibrosis), a comparison of the negative control group (G1) and positive control group (G2) showed that while virtually no activated HSCs (activated hepatic stellate cells, Ac-HSCs) were observed in the LETO rats (G1), a marked increase in Ac-HSGs was observed in the OLETF rats (G2) alone. Moreover, the increase in Ac-HSCs was moderately inhibited by monotherapy with obeticholic acid (G3) and losartan (G4), and the group administered the combination of both obeticholic acid and losartan (G5) showed complete inhibition to the same extent as in the negative control group (G1) (i.e., activation of HSC was virtually completely blocked).

FIG. 4 shows the results of a semiquantitative analysis of the immunohistochemical characteristics of the various groups. The α-SMA index (α-SI) shown on the vertical axis of the figure is the average area index of the α-SMA stained areas as calculated by computer analysis of the stained liver section images taken and collected from the rats in the various groups. This result quantitatively supports the results for immunohistolochemical characteristics seen in the micrographs of FIG. 3.

The α-SI values showed statistically significant differences among the various groups (p<0.01; Student's t-test). The positive control group (G2) showed extremely high α-SI values compared to the negative control group (G1). The obeticholic acid (G3) and losartan (G4) monotherapy groups showed moderate but significant decreases compared to the positive control group. Moreover, the group given combined administration of both obeticholic acid and losartan (G5) showed significant and pronounced decreases in α-SI values to the same level as in the negative control group (G1). This result, like the result of the histological analysis of working example 1 (i.e. inhibition of hepatic fibrosis), shows in a quantitatively and statistically significant manner that combined administration completely inhibits increases in Ac-HSCs, showing a highly pronounced synergistic effect compared to monotherapy with the respective drugs.

(2) Quantitative Analysis of TGF-β1 and Collagen mRNA Expression

Method

A comparative study was conducted by analyzing TGF-β1 and collagen (α1(I) procollagen) mRNA expression in the livers of the rates of the various groups of working example 1 by means of the quantitative real-time polymerase chain reaction (RT-PCR). Quantitation of the mRNA expression levels by RT-PCR was conducted on a StepOne Plus™ system (manufactured by Applied Biosystems®) using the fluorescent dye SYBR® Green Results The results are shown in FIG. 5.

FIG. 5 shows the results of RT-PCR quantitation of TGF-β1 and α1(I) procollagen mRNA expression in the various groups. The vertical axis in the figure indicates the amount of mRNA expression. Both TGF-β1 and α1(I) procollagen showed extremely high mRNA expression levels in the positive control group (G2) compared to the negative control group (G1). The respective obeticholic acid (G3) and losartan (G4) monotherapy groups showed a moderate decreasing tendency compared to the positive control group. Moreover, in the group administered a combination of obeticholic acid and losartan (G5), mRNA expression was significantly and markedly decreased. This result, like the result of the histological analysis of working example 1 (i.e. inhibition of hepatic fibrosis), shows in a quantitatively and statistically significant manner that combined administration inhibits increases in both TGF-β1 and α1(I) procollagen mRNA expression, showing a highly pronounced synergistic effect compared to monotherapy with the respective drugs.

Furthermore, Toll-like receptor 4 (TLR4) mRNA expression was quantitated by the same method. As was the case for the histological analysis result of working example 1 (i.e., inhibition of hepatic fibrosis), combined administration markedly inhibited increases in TLR4 mRNA expression (data not shown in the present specification). Hepatic TLR4-mediated intracellular signal transduction pathways (endotoxin LPS signal transduction) are known to play a major role in the mechanism of progression of hepatic fibrosis.

Working Example 3

Method

The various combined effects of obeticholic acid and three types of ARBs (losartan, valsartan, and candesartan) were confirmed in an in vitro cell system experiment. Specifically, using human hepatic stellate cells (HHSC), which are implicated in the main mechanism of progression of hepatic fibrosis in NASH, the effects of administration of obeticholic acid in combination with the three ARBs of inhibiting HHSC proliferation capacity and the expression of fibrosis markers were evaluated according to the following method.

Cells Used

Human hepatic stellate cells (HHSC) (also referred to as human hepatic star cells)

Drugs Used

Obeticholic acid (obtained from Intercept Pharmaceuticals, Inc. via Sumitomo Dainippon Pharma Co., Ltd.) was used as an FXR agonist, and commercial losartan (potassium salt of losartan; referred to in this working example simply as "losartan") and valsartan and candesartan (cilexitil ester of candesartan; referred to in this working example simply as "candesartan") were used as ARBs.

Reagents Used

Angiotensin II (AT-II) and/or lipopolysaccharide (LPS) were used (both AT1-mediated AT-II signalling and TLR4-mediated LPS signaling are known to play major roles in HSC activation and the progression of hepatic fibrosis).

Experimental Method (1) Study of Human Hepatic Stellate Cell (HHSC) Proliferation Inhibiting Effect The direct action of inhibiting HIISC proliferation capacity was evaluated by means of a cell proliferation assay using WST-1 reagent.
1) HHSCs were inoculated onto a 96-well plate in the amount of 3000 cells/200 µl and allowed to proliferate in 1% FBS DMEM medium for 24 hours.
2) After 24 hours, the cells were divided into the following 7 groups and transferred to culture medium after adding the following drugs and/or reagents. Losartan was used as an ARB.
Negative control group (G1): no drugs added (Control)
Positive control group A (G2A): AT-II ($10^{-6}$M)
Positive control group L (G2L): LPS $10^{-5}$M)
Positive control group AL (G2AL): ($10^{-6}$M)+LPS ($10^{-5}$M)
Obeticholic acid administration (G3): AT-II ($10^{-6}$M)+LPS ($10^{-5}$M)+obeticholic acid ($5\times10^{-6}$M)
ARB administration (G4): AT-II ($10^{-6}$M)+LPS ($10^{-5}$M)+ARB ($10^{-6}$M)
Obeticholic acid+ARB combined administration (G5): AT-II ($10^{-6}$M)+LPS ($10^{-5}$M)+obeticholic acid ($5\times10^{-6}$M)+ARB ($10^{-6}$M)
3) After the cells of the above groups (G1, G2A, G2L, G2AL, G3, G4, G5) were cultured for 24 hours, respective WST-1 cell proliferation assays were conducted, and the inhibitory effect of the pharmaceutical agents on cell proliferation was evaluated.

The inhibitory effect of valsartan and candesartan on HHSC proliferation was also evaluated according to steps 1)-3) above. Evaluations were conducted in the five groups G-1, G2AL, G3, G4, and G5.

(2) Study of Fibrosis Marker Gene Inhibiting Effect

With respect to the effect of inhibiting fibrosis marker gene expression, collagen production capacity and TGF-β production capacity were evaluated by the RT-PCR method.
1) HHSCs were inoculated onto a 6-well plate in the amount of 300,000 cells/2 ml and allowed to proliferate in 1% FBS DMEM medium for 24 hours.
2) After 24 hours, the cells were divided into the following 7 groups and transferred to culture medium after adding the following drugs and/or reagents. Losartan was used as an ARB.
Negative control group (G1): No drugs added (control)
Positive control group A (G2A): AT-II ($10^{-6}$M)
Positive control group L (G2L): LPS ($10^{-5}$M)
Positive control group AL (G2AL): ($10^{-6}$M)+LPS ($10^{-5}$M)
Obeticholic acid administration (G3): AT-II ($10^{-6}$M)+LPS ($10^{-5}$M)+obeticholic acid ($5\times10^{-6}$M)
ARB administration (G4): AT-II ($10^{-6}$M)+LPS ($10^{-5}$M)+ARB ($10^{-6}$M)
Obeticholic acid+ARB combined administration (G5): AT-II ($10^{-6}$M)+LPS ($10^{-5}$M)+obeticholic acid ($5\times10^{-6}$M)+ARB ($10^{-6}$M)
3) After the cells of the above groups (G1, G2A, G2L, G2AL, G3, G4, G5) were cultured for 24 hours, mRNA was extracted from the various groups. cDNA was obtained from the mRNA by reverse transcription, and fibrosis marker gene (TGF-β1 and α1(I) procollagen) expression was evaluated by the RT-PCR method The inhibitory effect of valsartan and candesartan on fibrosis marker gene expression was also evaluated according to steps 1)-3) above. Evaluations were conducted in the five groups G1, G2AL, G3, G4, and G5.

Results

The study results for inhibitory action on proliferation of human hepatic stellate cells (HHSC) are shown in FIG. 6-FIG. 8, and the results for inhibitory action on fibrosis marker gene expression are shown in FIG. 9-FIG. 14. The bars shown in the figures for the various groups indicate mean values±standard deviation (n=8). Asterisks indicate statistically significant differences among the study groups shown (*P<0.05, **P<0.01).

FIG. 6, FIG. 7 and FIG. 8 show the study results for the inhibitory action on HHSC proliferation capacity in the various groups using losartan, valsartan and candesartan as ARBs. The vertical axes of the figures indicate absorbance (absorption, OD), which strongly correlates with viable cell count. By measuring absorbance, the amount of formazan dye product produced by WST-1 reagent on metabolically active cells can be quantitated. As there is a linear positive correlation between formazan and the number of active cells in the culture medium, it becomes possible to observe cell proliferation capacity and cell viability.

Addition of the two reagents AT-II and LPS (G2AL) showed statistically significant promotion of proliferation of activated HHSC compared to the respective monotherapy groups (G2A and G2L) (FIG. 6).

The ARB monotherapy group (losartan, valsartan or candesartan) (G4) and the obeticholic acid and ARB (losartan, valsartan or candesartan) combined administration group (G5) showed statistically significant inhibition of promotion of activated HHSC proliferation by the two reagents AT-II and LPS compared to the positive control group AL (G2AL) (FIG. 6, FIG. 7 and FIG. 8).

FIG. 9, FIG. 10 and FIG. 11 show the results of a study of the effect of inhibiting TGF-β1 fibrosis marker gene expression in the various groups using losartan, valsartan, and candesartan as ARBs, and FIG. 12, FIG. 13 and FIG. 14 show the results of a study of the effect of inhibiting α1(I) procollagen fibrosis marker gene expression in the various groups using losartan, valsartan, and candesartan as ARBs. The vertical axes of the figures show the relative amount of mRNA expression.

TGF-β1 and α1(I)-procollagen (TLR4) mRNA expression induced by AT-II and LPS in the positive control group AL (G2AL) showed statistically significant inhibition for both the obeticholic acid monotherapy group (G3) and the ARB (losartan, valsartan or candesartan) monotherapy group. Moreover, in the group with addition of both obeticholic acid and an ARB (losartan, valsartan or candesartan) (G5), an effect of inhibiting TGE-β1 and α1(I)-procollagen mRNA expression was observed that was quite pronounced and statistically significant compared to the monotherapy groups (G3, G4).

The above results demonstrate that the combination of obeticholic acid and an ARB (losartan, valsartan or candesartan) has an outstanding preventive and therapeutic effect on NASH. In particular, a pronounced effect of preventing, inhibiting, and alleviating hepatic fibrosis in NASH can be expected. Moreover, the combination of obeticholic acid and an ARB or an FXR agonist and an ARB can also be expected to have an outstanding preventative and therapeutic effect on NASH.

Working Example 4

Using the same method as in working example 1, except that administration of the drugs, etc., was begun after the animals were administered porcine serum (PS) and hepatic fibrosis was allowed to progress for a specified period (such as 4 weeks), therapeutic effect was evaluated in the vehicle administration group (distilled water), administration groups, and combined administration group.

In pathologies involving more severe progression of fibrosis as well, as was the case in working example 1, an outstanding effect of preventing and treating NASH is expected.

Working Example 5

Using the same method as in working example 1, but with rats on a choline-deficient, 1-amino acid defined (CDAA) diet instead of OLETF rats as NASH model animals and rats on a choline-supplemented, 1-amino acid defined (CSAR) diet instead of LETO rats as a negative control group, therapeutic effect was evaluated in the vehicle administration group (distilled water), administration groups, and combined administration group.

In other NASH models as well, as was the case in working example 1, an outstanding effect of preventing and treating NASH is expected.

Working Example 6

Method

Using mice fed a methionine-choline-deficient (MCD) diet as a murine NASH model, the therapeutic effect of 0.5% carboxymethylcellulose (CMC) solution (vehicle administration group) and obeticholic acid (FXR agonist) and losartan (ARB) (administration groups, combined administration group) was evaluated by the following method.

Animals Used

Male C57Bl/6J mice (n=50-70)

Drugs Used

Obeticholic acid (obtained from Intercept Pharmaceuticals, Inc. via Sumitomo Dainippon Pharma Co., Ltd.) was used as an FXR agonist, and commercial losartan (potassium salt of losartan; referred to in this working example simply as "losartan") was used as an ARB.

Administered Dosage, Administration Period

Obeticholic acid (3-30 mg/kg/day) and/or losartan (0.1-30 mg/kg/day) was/were given by forced oral administration; the administration period was 1 to 6 weeks in all cases.

Experimental Method

After 6- to 12-week-old C57Bl/6J mice were fed an MCD diet for 0 to 5 weeks, they were randomly divided into 4 groups (G2, G3, G4, G5) (n=10 for each group). In the same manner, 6- to 12-week-old C57Bl/6J mice (n=10) were given ordinary feed and taken as group G1. Beginning on the day the MCD diet was begun or 3-5 weeks thereafter, the group G3 and G4 mice were respectively administered obeticholic acid (3-30 mg/kg/day) and losartan (0.1-30 mg/kg/day) daily for 1-3 weeks by forced continuous oral administration. The group G5 mice were given daily combined administration of obeticholic acid (3-30 mg/kg/day) and losartan (0.1-30 mg/kg/day) for 1-6 weeks in the same manner. The mice in the G1 group (ordinary feed group) and G2 group (MCD group) were administered 0.5% CMC solution as a vehicle instead of the drugs and taken as the negative control group and positive control group respectively (with the same administration method as in the drug groups).

Histological Analysis

In order to evaluate the progression of hepatic fibrosis, formalin-fixed paraffin-embedded liver sections (5 µm in width) were taken from mice that had completed the above testing and stained with Sirius Red. Micrographs of the stained sections were taken and collected (in all of the mice, microscopic images were collected with multiple fields per sample), and the micrographs of the various groups were compared. In order to quantitate the progression of fibrosis in the various groups, a semiquantitative analysis of the histological characteristics of the images of the stained specimens collected was conducted using analysis software. Moreover, the liver specimens (5 µm in width) were stained with Oil Red O, micrographs of the stained sections were taken and collected in the same manner, and the images were compared among the groups. In order to quantitate the extent of the progression of fatty tissue degeneration in the various groups, a semiquantitative analysis of the histological characteristics of the images of the stained specimens collected was conducted using analysis software. Alternatively, fibrosis factors were measured using mRNA extracted from the liver using the semiquantitative reverse-transcriptase polymerase chain reaction (RT-PCR) method.

In other NASH models as well, as was the case in working examples 1, 4 and 5, an outstanding effect of preventing and treating NASH is expected.

Working Example 8

The accepted pathological diagnostic criterion for NASH is "observation of liver cell ballooning accompanied by inflammation in addition to large-droplet hepatic steatosis." Matteoni et al. conducted a long-term follow-up study of patients with NAFLD, classifying the disease based on pathology findings into 4 types (type 1: fatty liver alone, type 2: fat accumulation plus inflammatory cell infiltration, type 3: fat accumulation plus ballooning hepatocyte degeneration, type 4: fat accumulation/ballooning hepatocyte degeneration plus Mallory-Denk bodies or fibrosis). Their results showed that compared to types 1 and 2, progression to liver cirrhosis and liver-disease related deaths were significantly more frequent in patients with types 3 and 4, indicating that pathological classification is of great clinical importance. In order to reduce differences among individual observers and institutions, the Nonalcoholic Steatohepatitis Clinical Research Network has proposed a pathodiagnostic scoring system in which the extent of fatty degeneration, inflammation, and hepatocyte ballooning is scored (NAS: NAFLD Activity Score) (Matteoni C A, Younossi Z M, Gramlich T, Boparai N, Liu Y C, McCullough A J: Nonalcoholic fatty liver disease: A spectrum of clinical and pathological severity. Gastroenterology, 116; 1413-1419, 1999). The pathodiagnostic standards making up the NASH score were evaluated using the following animal model, and the individual and combined effects of an FXR agonist (obeticholic acid) and an ARB (losartan) were studied.

Method

Using mice fed a choline-deficient, amino acid-defined, high-fat diet (CDAHFD) with reduced methionine as a murine NASH model, the therapeutic effect of 0.5% methylcellulose (MC) solution (vehicle administration group) and obeticholic acid (FXR agonist) and losartan (ARB) (administration groups, combined administration group) was evaluated by the following method.

Animals Used

Male C57Bl/6J mice (n=49)

Drugs Used

Obeticholic acid (obtained from Intercept Pharmaceuticals, Inc. via Sumitomo Dainippon Pharma Co., Ltd.) was used as an FXR agonist, and commercial losartan (potassium salt of losartan; referred to in this working example simply as "losartan") was used as an ARB.

Administered Dosage, Administration Period

Obeticholic acid (30 mg/kg/day) and/or losartan (30 mg/kg/day) was/were given by forced oral administration; the total administration period was 3 weeks.

Experimental Method

After 6-week-old C57Bl/6J mice were fed a CDAHFD for 0 to 2.5 weeks, they were randomly divided into 4 groups (G2, G3, G4, G5) (n=10 for each group). In the same manner, 6-week-old C57Bl/6J mice (n=13) were given ordinary feed and taken as group G1. Beginning 2.5 weeks after the CDAHFD was started, the group G3 and G4 mice were respectively administered obeticholic acid (30 mg/kg/day) and losartan (30 mg/kg/day) daily for 3 weeks by forced continuous oral administration. The group G5 mice were given daily combined administration of obeticholic acid (30 mg/kg/day) and losartan (30 mg/kg/day) for 3 weeks in the same manner. The mice in the group (ordinary feed group) and G2 group (CDAHFD group) were administered 0.5% MC solution as a vehicle instead of the drugs and taken as the negative and positive control group respectively (with the same administration method as in the drug groups).

Histological Analysis

In order to evaluate the progression of hepatic fibrosis, formalin-fixed paraffin-embedded liver sections (3 μm in width) were taken from mice that had completed the above testing and subjected to hematoxylin and eosin staining. Micrographs of the stained sections were taken and collected (in all of the mice, microscopic images were collected with multiple fields per sample), and the micrographs of the various groups were compared. In order to quantitate the extent of NAS in the various groups, a semiquantitative analysis of the histological characteristics of the images of the stained specimens collected was conducted using analysis software. With respect to liver cell swelling (swelling to approximately 1.5 times the diameter of normal liver cells or more), an indicator similar to liver cell fatty degeneration and ballooning, the area ratios occupied by the lesions were graded. With respect to inflammation, the number of agglomeration foci containing 5 or more inflammatory cells per unit area was graded. The total of these grades was defined as NAS.

Results

FIG. 15 shows the results of a study of the action of administration on improving liver cell swelling in a NASH model of mice fed a CDAHFD. The vertical axis of the graph shows the positive area rate of liver cell swelling (liver cell swelling improvement rate: %) in the various administration groups (G3, G4, G5) taking the difference between the negative control group (G1) and the positive control group (G2) as 100%. The significantly increased liver cell swelling in the positive control group (G2) tended to be inhibited in the obeticholic acid monotherapy group (G3). The losartan monotherapy group (G4) showed no improving tendency whatsoever. Surprisingly, moreover, in the group administered a combination of obeticholic acid and losartan (G5), liver cell swelling was improved, with a statistically significant difference being observed. This effect in the combined administration group (G5) was extremely pronounced compared to the respective monotherapy groups (G3, G4), and this can be said to constitute an unanticipated synergistic effect.

The improvement in the positive area rate of liver cell swelling showed a statistically significant difference only in the G5 group ($P<0.01$; nonparametric Dunnett test). This result shows that the effect of improving liver cell swelling of combined administration is extremely pronounced and synergistic compared to monotherapy with the individual agents, with this effect being both quantitatively and statistically significant.

An improving action was also observed in liver cell fatty degeneration and NASH in the G5 group in particular, as was the case in evaluation of liver cell swelling.

Working Example 8

According to the NASH/NAFLD Practice Guideline of 2015 (Japan Society of Hepatology, NASH/NAFLD Practice Guideline 2015. Tokyo: Bunkodo; 2015.), the important factors in NASH diagnostic screening are an abdominal ultrasound diagnosis of fatty liver and abnormal ALT (alanine aminotransferase) values. The diagnosis of NASH is confirmed by liver biopsy, with control of obesity/hypertension/lipid abnormalities being one of the basic criteria, and continuing high values for transaminases (aminotransferases) are also significant. Moreover, NASH shows a tendency to progress rapidly in patients with high ALT levels. On the other hand, according to the PIVENS study, which examined the efficacy and safety of vitamin E in patients with NASH, taking cases in which ALT decreased to 40

IU/L or less or in which ALT decreased by 30% or more compared to baseline as ALT responders, NASH was found to be significantly improved in the ALT responders compared to the ALT non-responders in the vitamin E group, with no improvement in NASH in the placebo group, and significant improvement in fibrosis was also reported (Hoofnagle J H, Van Natta M L, Kleiner D E, Clark J M, Kowdley K V, Loomba R, et al. Vitamin E and changes in serum alanine aminotransferase levels in patients with nonalcoholic steatohepatitis. Aliment Pharmacol Ther. 2013 Jul. 38 (2): 134-43). Based on the above findings, as ALT is considered an important prognostic factor in the progression of NASH, treatment to improve ALT levels is expected to alleviate the pathology of NASH. For this reason, evaluation was conducted using the animal model of reduction of ALT below, and the effects of monotherapy and combined administration of an FXR agonist (obeticholic acid) and an ARB (losartan) were studied.

Method

The same method was used as in working example 7.

Animals Used

Male C57Bl/6J mice (n=50)

Drugs Used

The same drugs were used as in working example 7.

Administered Dosage, Administration Period

Obeticholic acid (10 mg/kg/day) and/or losartan (30 mg/kg/day) was/were given by forced oral administration; the total administration period was 3 weeks.

Experimental Method

After 6-week-old C57Bl/6J mice were fed a CDAHFD for 0-6 weeks, they were randomly divided into 4 groups (G2, G3, G4, G5) (n=10 for each group). In the same manner, 6-week-old C57Bl/6J mice (n=10) were given ordinary feed and taken as group G1. Beginning 6 weeks after the CDAHFD was started, the group G3 and G4 mice were respectively administered obeticholic acid (10 mg/kg/day) and losartan (30 mg/kg/day) daily for 3 weeks by forced continuous oral administration. The group G5 mice were given daily combined administration of obeticholic acid (10 mg/kg/day) and losartan (30 mg/kg/day) for 3 weeks in the same manner. The mice in the G1 group (ordinary feed group) and G2 group (CDAHFD group) were administered 0.5% CMC solution as a vehicle instead of the drugs and taken as the negative and positive control group respectively (with the same administration method as in the drug groups).

Biochemical Tests

In order to evaluate serum alanine aminotransferase (ALT) activity, blood samples were taken from mice that had completed the above-mentioned testing, and the serum was separated. Using a pharmaceutical product for in vitro diagnosis, ALT activity in the serum samples was enzymatically measured.

Results

FIG. 16 shows the results of a study of the effect of drug administration of improving ALT activity in a NASH model of animals placed on the CDAHFD.

FIG. 16 shows the change in ALT activity (ΔU/L; negative value indicates improvement) in the drug administration groups (G3, G4, G5) based on average ALT activity in the positive control group (G2). Compared to the negative control group (G1), ALT activity showed a statistically significant increase in the positive control group (G2), while only an improving trend was seen in the obeticholic acid monotherapy (G3) and losartan monotherapy (G4) groups, with no statistically significant improvement being observed. Surprisingly, the group given combined administration of both obeticholic acid and losartan (G5) showed a statistically significant difference in improvement in ALT activity. This effect in the combined administration group (G5) was extremely pronounced compared to the respective monotherapy groups (G3, G4), and this can be said to constitute an unanticipated synergistic effect.

For improvement in ALT activity, a statistically significant difference was observed only in the G5 group (p<0.01; nonparametric Dunnett test). This result shows that the effect of alleviating liver injury of combined administration is extremely pronounced and synergistic compared to monotherapy with the individual agents, with this effect being both quantitatively and statistically significant.

Working Example 9

Using obeticholic acid as an FXR agonist and candesartan, telmisartan, valsartan, olmesartan, irbesartan or azilsartan instead of losartan as an ARB, therapeutic effect was evaluated in the vehicle administration group (distilled water), administration groups, and combined administration group according to the same method as in working examples 1, 2 and 4-8. Moreover, using obeticholic acid as an FXR agonist and teltnisartan, olmesartan, irbesartan or azilsartan instead of losartan, valsartan or candesartan as an ARB, the combined effect of FXR agonists and ARBs was confirmed according to the same method as in working example 3.

The combination of obeticholic acid and an ARB, like the combination of obeticholic acid and losartan, is expected to have an outstanding effect of preventing and treating NASH.

Working Example 10

Using chenodeoxycholic acid, INT-767, LY-2562175, Px-104 or LJN-452 instead of obeticholic acid as an FXR agonist and losartan as an ARB, and according to the same method as in working examples 1, 2 and 4-8, therapeutic effect was evaluated in the vehicle administration group (distilled water), administration groups, and combined administration group. Moreover, using chenodeoxycholic acid, INT-767, LY-2562175, Px-104 or LJN-452 instead of obeticholic acid as an FXR agonist and losartan as an ARB, the combined effect of FXR agonists and ARBs was confirmed according to the same method as in working example 3.

Combinations of other FXR agonists and losartan as well, like the combination of obeticholic acid and losartan, are expected to have an outstanding effect of preventing and treating NASH.

Working Example 11

Using chenodeoxycholic acid, INT-767, LY-2562175, Px-104 or LJN-452 instead of obeticholic acid as an FXR agonist and losartan as an ARB, the therapeutic effect of candesartan, telmisartan, valsartan, olmesartan, irbesartan or azilsartan was evaluated in the vehicle administration group (distilled water), administration groups, and combined administration group according to the same method as in working examples 1, 2, and 4-8. Moreover, using chenodeoxycholic acid, INT-767, LY-2562175, Px-104 or LJN-452 instead of obeticholic acid as an FXR agonist and telmisartan, oltnesartan, irbesartan or azilsartan instead of losartan, valsartan or candesartan as an ARB, the combined effect of FXR agonists and ARBs was confirmed according to the same method as in working example 3.

Combinations of other FXR agonists and ARBs as well, like the combination of obeticholic acid and losartan, are expected to have an outstanding effect of preventing and treating NASH.

INDUSTRIAL APPLICABILITY

The combination pharmaceutical agent of the present invention is useful in the prevention and/or treatment of liver disease, particularly NASH. Moreover, it is useful in all liver diseases, particularly in the prevention, inhibition, and/or alleviation of hepatic fibrosis in NASH.

The invention claimed is:

1. A pharmaceutical composition comprising a combination of obeticholic acid or a pharmaceutically acceptable salt thereof in the amount of 2 mg-100 mg and losartan or a pharmaceutically acceptable salt thereof in the amount of 5 mg-100 mg, wherein the obeticholic acid or pharmaceutically acceptable salt thereof and losartan or pharmaceutically acceptable salt thereof are the only active pharmaceutical ingredients present in the composition.

2. The pharmaceutical composition of claim 1, comprising one or more pharmaceutically acceptable carriers or excipients.

3. The pharmaceutical composition of claim 1, comprising obeticholic acid or a pharmaceutically acceptable salt thereof in the amount of 5 mg-50 mg.

4. The pharmaceutical composition of claim 1, comprising losartan or a pharmaceutically acceptable salt thereof in the amount of 10 mg-50 mg.

5. The pharmaceutical composition of claim 1, comprising obeticholic acid or a pharmaceutically acceptable salt thereof in the amount of 5 mg-50 mg and losartan or a pharmaceutically acceptable salt thereof in the amount of 10 mg-50 mg.

* * * * *